US009173973B2

(12) United States Patent
Thatcher et al.

(10) Patent No.: US 9,173,973 B2
(45) Date of Patent: *Nov. 3, 2015

(54) BIOABSORBABLE POLYMERIC COMPOSITION FOR A MEDICAL DEVICE

(76) Inventors: G. Lawrence Thatcher, Chelmsford, MA (US); Robert J. Cottone, Davie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,394

(22) Filed: Feb. 10, 2012

(65) Prior Publication Data

US 2012/0142869 A1 Jun. 7, 2012

Related U.S. Application Data

(60) Continuation of application No. 12/508,442, filed on Jul. 23, 2009, now Pat. No. 8,137,603, which is a division of application No. 11/781,230, filed on Jul. 20, 2007, now Pat. No. 7,846,361.

(60) Provisional application No. 60/862,433, filed on Oct. 20, 2006, provisional application No. 60/807,932, filed on Jul. 20, 2006.

(51) Int. Cl.
B29C 47/00 (2006.01)
A61L 27/26 (2006.01)
A61L 27/18 (2006.01)
A61L 31/06 (2006.01)
(Continued)

(52) U.S. Cl.
CPC ............... *A61L 27/26* (2013.01); *A61L 27/18* (2013.01); *A61L 27/58* (2013.01); *A61L 31/06* (2013.01); *B29C 47/0066* (2013.01); B29C 2793/009 (2013.01); B29C 2793/0018 (2013.01); B29K 2067/046 (2013.01); B29K 2105/0085 (2013.01); B29K 2995/006 (2013.01); B29L 2031/7534 (2013.01); C08L 2203/02 (2013.01); C08L 2205/02 (2013.01); Y10T 428/139 (2015.01); Y10T 428/1352 (2015.01)

(58) Field of Classification Search
CPC .......... A61L 27/18; A61L 31/06; C08L 67/04
USPC ....................... 623/1.15; 264/150, 154, 209.1
See application file for complete search history.

(56) References Cited

U.S. PATENT DOCUMENTS 4,057,537 A 11/1977 Sinclair
4,243,775 A 1/1981 Rosensaft et al.
(Continued)

FOREIGN PATENT DOCUMENTS

CN 1509315 A 6/2004
EP 0272902 A2 6/1988
(Continued)

OTHER PUBLICATIONS

European Search Report 07799753 dated Jun. 4, 2014.
(Continued)

*Primary Examiner* — Richard Crispino
*Assistant Examiner* — Robert Dye
(74) *Attorney, Agent, or Firm* — Ascenda Law Group PC

(57) ABSTRACT

A biodegradable and biocompatible nontoxic polymeric composition is provided which includes a base material such as a crystallizable polymer, copolymer, or terpolymer, and a copolymer or terpolymer additive. Medical devices manufactured from the composition are also provided.

5 Claims, 10 Drawing Sheets

(51) Int. Cl.
*A61L 27/58* (2006.01)
*B29K 67/00* (2006.01)
*B29K 105/00* (2006.01)
*B29L 31/00* (2006.01)

(56) References Cited

U.S. PATENT DOCUMENTS

| | | | |
|---|---|---|---|
| 4,300,565 | A | 11/1981 | Rosensaft et al. |
| 4,379,138 | A | 4/1983 | Pitt et al. |
| 4,650,488 | A | 3/1987 | Bays et al. |
| 4,655,777 | A | 4/1987 | Dunn et al. |
| 4,719,246 | A | 1/1988 | Murdoch et al. |
| 4,810,775 | A | 3/1989 | Bendix et al. |
| 4,916,193 | A | 4/1990 | Tang et al. |
| 4,938,763 | A | 7/1990 | Dunn et al. |
| 4,944,974 | A | 7/1990 | Zachariades |
| 4,968,317 | A | 11/1990 | Tormala et al. |
| 5,066,772 | A | 11/1991 | Tang |
| 5,097,005 | A | 3/1992 | Tietz |
| 5,142,023 | A | 8/1992 | Gruber et al. |
| 5,145,945 | A | 9/1992 | Tang et al. |
| 5,185,408 | A | 2/1993 | Tang et al. |
| 5,225,129 | A | 7/1993 | Van Den Berg |
| 5,225,521 | A | 7/1993 | Spinu |
| 5,256,764 | A | 10/1993 | Tang et al. |
| 5,274,074 | A | 12/1993 | Tang et al. |
| 5,290,494 | A | 3/1994 | Coombes et al. |
| 5,320,624 | A | 6/1994 | Kaplan et al. |
| 5,322,925 | A | 6/1994 | Muth et al. |
| 5,342,395 | A | 8/1994 | Jarrett et al. |
| 5,378,792 | A | 1/1995 | Sterzel |
| 5,412,068 | A | 5/1995 | Tang et al. |
| 5,475,063 | A | 12/1995 | Kaplan et al. |
| 5,486,593 | A | 1/1996 | Tang et al. |
| 5,492,997 | A | 2/1996 | Grijpma et al. |
| 5,525,646 | A | 6/1996 | Lundgren et al. |
| 5,536,807 | A | 7/1996 | Gruber et al. |
| 5,578,325 | A | 11/1996 | Domb et al. |
| 5,665,428 | A | 9/1997 | Cha et al. |
| 5,665,831 | A | 9/1997 | Neuenschwander et al. |
| 5,670,161 | A | 9/1997 | Healy et al. |
| 5,691,424 | A | 11/1997 | Suzuki et al. |
| 5,700,901 | A * | 12/1997 | Hurst et al. .................. 528/354 |
| 5,716,396 | A | 2/1998 | Williams, Jr. |
| 5,739,176 | A | 4/1998 | Dunn et al. |
| 5,792,400 | A | 8/1998 | Talja et al. |
| 5,827,322 | A | 10/1998 | Williams |
| 5,834,582 | A | 11/1998 | Sinclair et al. |
| 5,849,374 | A | 12/1998 | Gruber et al. |
| 5,849,401 | A | 12/1998 | El-Afandi et al. |
| 5,916,950 | A | 6/1999 | Obuchi et al. |
| 5,925,061 | A | 7/1999 | Ogi |
| 5,948,016 | A | 9/1999 | Jang |
| 5,990,194 | A | 11/1999 | Dunn et al. |
| 6,033,433 | A | 3/2000 | Her |
| 6,107,453 | A | 8/2000 | Zuccato et al. |
| 6,165,217 | A | 12/2000 | Hayes |
| 6,221,958 | B1 | 4/2001 | Shalaby et al. |
| 6,228,111 | B1 | 5/2001 | Tormala et al. |
| 6,297,349 | B1 | 10/2001 | Goldberg et al. |
| 6,306,424 | B1 | 10/2001 | Vyakarnam et al. |
| 6,333,029 | B1 | 12/2001 | Vyakarnam et al. |
| 6,338,739 | B1 | 1/2002 | Datta et al. |
| 6,346,599 | B1 | 2/2002 | Goldberg et al. |
| 6,350,464 | B1 | 2/2002 | Dang |
| 6,352,667 | B1 | 3/2002 | English |
| 6,355,699 | B1 | 3/2002 | Vyakarnam et al. |
| 6,361,789 | B1 | 3/2002 | Zuccato et al. |
| 6,365,149 | B2 | 4/2002 | Vyakarnam et al. |
| 6,365,173 | B1 | 4/2002 | Domb |
| 6,413,539 | B1 | 7/2002 | Shalaby |
| 6,511,505 | B2 * | 1/2003 | Cox et al. .................. 623/1.16 |
| 6,511,748 | B1 | 1/2003 | Barrows |
| 6,534,084 | B1 | 3/2003 | Vyakarnam et al. |
| 6,537,585 | B1 | 3/2003 | Dang et al. |
| 6,572,894 | B2 | 6/2003 | Rossling et al. |
| 6,575,688 | B2 | 6/2003 | Mehdianpour |
| 6,607,548 | B2 * | 8/2003 | Pohjonen et al. ............. 606/230 |
| 6,623,521 | B2 | 9/2003 | Steinke et al. |
| 6,730,772 | B2 | 5/2004 | Shastri |
| 6,740,731 | B2 | 5/2004 | Bigg et al. |
| 6,747,121 | B2 | 6/2004 | Gogolewski |
| 6,794,484 | B2 | 9/2004 | Newman, Jr. et al. |
| 6,916,483 | B2 | 7/2005 | Ralph et al. |
| 6,991,647 | B2 | 1/2006 | Jadhav |
| 7,001,328 | B1 | 2/2006 | Barofsky et al. |
| 7,112,417 | B2 | 9/2006 | Vyakarnam et al. |
| 7,160,592 | B2 | 1/2007 | Rypacek et al. |
| 7,264,641 | B2 | 9/2007 | Prasad |
| 7,291,166 | B2 | 11/2007 | Cheng et al. |
| 7,291,345 | B2 | 11/2007 | Winterbottom et al. |
| 7,297,102 | B2 | 11/2007 | Smith et al. |
| 7,326,245 | B2 | 2/2008 | Rosenthal |
| 7,833,260 | B2 | 11/2010 | Cottone et al. |
| 7,846,197 | B2 | 12/2010 | Cottone et al. |
| 7,846,361 | B2 | 12/2010 | Thatcher et al. |
| 7,897,224 | B2 | 3/2011 | Thatcher et al. |
| 7,959,942 | B2 | 6/2011 | Cottone |
| 8,137,603 | B2 * | 3/2012 | Thatcher et al. ........... 264/209.1 |
| 8,460,362 | B2 | 6/2013 | Cottone et al. |
| 8,460,364 | B2 | 6/2013 | Cottone et al. |
| 8,642,068 | B2 | 2/2014 | Cottone |
| 8,642,707 | B2 | 2/2014 | Thatcher et al. |
| 2001/0000189 | A1 | 4/2001 | Hayes |
| 2001/0000352 | A1 | 4/2001 | Hayes |
| 2001/0012940 | A1 | 8/2001 | Tunc |
| 2001/0021871 | A1 | 9/2001 | Stinson |
| 2001/0029398 | A1 | 10/2001 | Jadhav |
| 2001/0033857 | A1 | 10/2001 | Vyakarnam et al. |
| 2001/0038854 | A1 | 11/2001 | Hata et al. |
| 2001/0043913 | A1 | 11/2001 | Spaans et al. |
| 2001/0044413 | A1 | 11/2001 | Pierce et al. |
| 2001/0044514 | A1 | 11/2001 | Baker et al. |
| 2001/0044567 | A1 | 11/2001 | Zamora et al. |
| 2001/0051833 | A1 | 12/2001 | Walter et al. |
| 2002/0005600 | A1 | 1/2002 | Ma |
| 2002/0028911 | A1 | 3/2002 | Barnette et al. |
| 2002/0032488 | A1 | 3/2002 | Brekke et al. |
| 2002/0099434 | A1 | 7/2002 | Buscemi et al. |
| 2002/0106406 | A1 | 8/2002 | McHugh et al. |
| 2002/0123546 | A1 | 9/2002 | Bigg et al. |
| 2002/0137706 | A1 | 9/2002 | Evans et al. |
| 2002/0150604 | A1 | 10/2002 | Yi et al. |
| 2002/0151617 | A1 | 10/2002 | Mao et al. |
| 2002/0151650 | A1 | 10/2002 | Pathak et al. |
| 2002/0155092 | A1 | 10/2002 | Leong et al. |
| 2002/0161400 | A1 | 10/2002 | Demopulos et al. |
| 2002/0168338 | A1 | 11/2002 | Baird |
| 2002/0173595 | A1 | 11/2002 | Pohjonen et al. |
| 2002/0188347 | A1 | 12/2002 | Mathis |
| 2002/0192294 | A1 | 12/2002 | Albayrak |
| 2002/0192449 | A1 | 12/2002 | Hobbs et al. |
| 2003/0009004 | A1 | 1/2003 | Nam et al. |
| 2003/0014127 | A1 | 1/2003 | Talja et al. |
| 2003/0049320 | A1 | 3/2003 | Bhagwatwar et al. |
| 2003/0050426 | A1 | 3/2003 | Shastri |
| 2003/0050687 | A1 | 3/2003 | Schwade et al. |
| 2003/0060595 | A1 | 3/2003 | Rafler et al. |
| 2003/0060836 | A1 | 3/2003 | Wang et al. |
| 2003/0069629 | A1 * | 4/2003 | Jadhav et al. ................ 623/1.15 |
| 2003/0082148 | A1 | 5/2003 | Ludwig et al. |
| 2003/0083732 | A1 | 5/2003 | Stinson |
| 2003/0083745 | A1 | 5/2003 | Pohjonen et al. |
| 2003/0114637 | A1 | 6/2003 | Gogolewski |
| 2003/0134099 | A1 | 7/2003 | Barrows |
| 2003/0138493 | A1 | 7/2003 | Dang |
| 2003/0144570 | A1 | 7/2003 | Hunter et al. |
| 2003/0147934 | A1 | 8/2003 | Hissink et al. |
| 2003/0149474 | A1 | 8/2003 | Becker |
| 2003/0153965 | A1 | 8/2003 | Supronowicz et al. |
| 2003/0161881 | A1 | 8/2003 | Hansen et al. |
| 2003/0191449 | A1 | 10/2003 | Nash et al. |
| 2003/0195611 | A1 | 10/2003 | Greenhalgh et al. |
| 2003/0208259 | A1 | 11/2003 | Penhasi |

(56) References Cited

U.S. PATENT DOCUMENTS

| | | |
|---|---|---|
| 2003/0211135 A1 | 11/2003 | Greenhalgh et al. |
| 2003/0212449 A1 | 11/2003 | Cox |
| 2003/0216496 A1 | 11/2003 | Mohanty et al. |
| 2003/0219562 A1 | 11/2003 | Rypacek et al. |
| 2003/0229391 A1 | 12/2003 | Thompson |
| 2003/0229393 A1 | 12/2003 | Kutryk et al. |
| 2003/0236573 A1 | 12/2003 | Evans et al. |
| 2004/0002580 A1 | 1/2004 | Newman, Jr. et al. |
| 2004/0006146 A1 | 1/2004 | Evans et al. |
| 2004/0006199 A1 | 1/2004 | Newman, Jr. et al. |
| 2004/0009226 A1 | 1/2004 | McHugh et al. |
| 2004/0013703 A1 | 1/2004 | Ralph et al. |
| 2004/0013730 A1 | 1/2004 | Saxena et al. |
| 2004/0014929 A1 | 1/2004 | Lendlein et al. |
| 2004/0024143 A1 | 2/2004 | Lendlein et al. |
| 2004/0029750 A1 | 2/2004 | Schudel et al. |
| 2004/0030380 A1 | 2/2004 | Shulze et al. |
| 2004/0030408 A1 | 2/2004 | Griffin et al. |
| 2004/0039441 A1 | 2/2004 | Rowland et al. |
| 2004/0054372 A1 | 3/2004 | Corden et al. |
| 2004/0058140 A1 | 3/2004 | Hobbs et al. |
| 2004/0071774 A1 | 4/2004 | Dang |
| 2004/0088044 A1 | 5/2004 | Brown |
| 2004/0089602 A1 | 5/2004 | Heinrich et al. |
| 2004/0098090 A1 | 5/2004 | Williams |
| 2004/0122174 A1 | 6/2004 | Mather et al. |
| 2004/0137033 A1 | 7/2004 | Calhoun et al. |
| 2004/0138738 A1 | 7/2004 | Stinson |
| 2004/0156906 A1 | 8/2004 | Ding et al. |
| 2004/0157967 A1 | 8/2004 | Ito |
| 2004/0161442 A1 | 8/2004 | Zamora et al. |
| 2004/0210218 A1 | 10/2004 | Dixon et al. |
| 2004/0214983 A1 | 10/2004 | Tobita et al. |
| 2004/0215218 A1 | 10/2004 | Demopulos et al. |
| 2004/0220660 A1 | 11/2004 | Shanley et al. |
| 2004/0247644 A1 | 12/2004 | Bratt et al. |
| 2004/0249442 A1 | 12/2004 | Fleming |
| 2004/0253290 A1 | 12/2004 | Kim et al. |
| 2004/0260318 A1 | 12/2004 | Hunter et al. |
| 2005/0001358 A1 | 1/2005 | Nakazawa et al. |
| 2005/0008672 A1 | 1/2005 | Winterbottom et al. |
| 2005/0021131 A1 | 1/2005 | Venkatraman et al. |
| 2005/0025808 A1 | 2/2005 | Herrmann et al. |
| 2005/0042253 A1 | 2/2005 | Farrar et al. |
| 2005/0058632 A1 | 3/2005 | Hendrick et al. |
| 2005/0112171 A1 | 5/2005 | Tang et al. |
| 2005/0112172 A1 | 5/2005 | Pacetti |
| 2005/0118238 A1 | 6/2005 | Zhu et al. |
| 2005/0119720 A1 | 6/2005 | Gale et al. |
| 2005/0123588 A1 | 6/2005 | Zhu et al. |
| 2005/0131528 A1 | 6/2005 | Buscemi et al. |
| 2005/0136259 A1 | 6/2005 | Mohanty et al. |
| 2005/0142163 A1 | 6/2005 | Hunter et al. |
| 2005/0147562 A1 | 7/2005 | Hunter et al. |
| 2005/0147643 A1 | 7/2005 | Hunter et al. |
| 2005/0161857 A1 | 7/2005 | Coombes et al. |
| 2005/0161859 A1 | 7/2005 | Miller et al. |
| 2005/0165142 A1 | 7/2005 | Nishimura et al. |
| 2005/0165206 A1 | 7/2005 | Rafler et al. |
| 2005/0169958 A1 | 8/2005 | Hunter et al. |
| 2005/0171299 A1 | 8/2005 | Shalaby |
| 2005/0175665 A1 | 8/2005 | Hunter et al. |
| 2005/0181011 A1 | 8/2005 | Hunter et al. |
| 2005/0186261 A1 | 8/2005 | Avelar et al. |
| 2005/0187605 A1 | 8/2005 | Greenhalgh et al. |
| 2005/0196420 A1 | 9/2005 | Zucherman et al. |
| 2005/0202067 A1 | 9/2005 | Lendlein et al. |
| 2005/0209603 A1 | 9/2005 | Zucherman et al. |
| 2005/0232966 A1 | 10/2005 | Hughes et al. |
| 2005/0238722 A1 | 10/2005 | Pathak et al. |
| 2005/0240137 A1 | 10/2005 | Zhu et al. |
| 2005/0244353 A1 | 11/2005 | Lendlein et al. |
| 2005/0244475 A1 | 11/2005 | Edelman et al. |
| 2005/0244538 A1 | 11/2005 | Andersen et al. |
| 2005/0245637 A1 | 11/2005 | Hossainy et al. |
| 2005/0246021 A1 | 11/2005 | Ringeisen et al. |
| 2005/0249697 A1 | 11/2005 | Uhrich et al. |
| 2005/0260247 A1 | 11/2005 | Ralph et al. |
| 2005/0271701 A1 | 12/2005 | Cottone et al. |
| 2005/0281856 A1 | 12/2005 | McGlohorn et al. |
| 2005/0283229 A1 | 12/2005 | Dugan et al. |
| 2005/0288771 A1 | 12/2005 | Majercak |
| 2006/0004437 A1 | 1/2006 | Jayaraman |
| 2006/0008504 A1 | 1/2006 | Kerr et al. |
| 2006/0018942 A1 | 1/2006 | Rowe et al. |
| 2006/0025649 A1 | 2/2006 | Smith et al. |
| 2006/0040894 A1 | 2/2006 | Hunter et al. |
| 2006/0041102 A1* | 2/2006 | Hossainy et al. ............. 528/354 |
| 2006/0047095 A1 | 3/2006 | Pacetti |
| 2006/0051455 A1 | 3/2006 | Andersen et al. |
| 2006/0062821 A1 | 3/2006 | Simhambhatla et al. |
| 2006/0067908 A1 | 3/2006 | Ding |
| 2006/0074191 A1 | 4/2006 | Desnoyer et al. |
| 2006/0083767 A1 | 4/2006 | Deusch et al. |
| 2006/0093771 A1 | 5/2006 | Rypacek et al. |
| 2006/0115449 A1 | 6/2006 | Pacetti |
| 2006/0140892 A1 | 6/2006 | Lendlein et al. |
| 2006/0147491 A1 | 7/2006 | DeWitt et al. |
| 2006/0154195 A1 | 7/2006 | Mather et al. |
| 2006/0160985 A1 | 7/2006 | Pacetti et al. |
| 2006/0177495 A1 | 8/2006 | Allen et al. |
| 2006/0178477 A1 | 8/2006 | Neuenschwander |
| 2006/0188486 A1 | 8/2006 | Carpenter et al. |
| 2006/0204738 A1 | 9/2006 | Dubrow et al. |
| 2006/0224226 A1 | 10/2006 | Huang et al. |
| 2006/0233887 A1 | 10/2006 | Day |
| 2006/0240078 A1 | 10/2006 | Jenkins et al. |
| 2006/0246108 A1 | 11/2006 | Pacetti et al. |
| 2006/0258834 A1 | 11/2006 | Van Der Wal et al. |
| 2006/0265048 A1* | 11/2006 | Cheng et al. ................. 623/1.15 |
| 2006/0269586 A1 | 11/2006 | Pacetti |
| 2006/0271170 A1 | 11/2006 | Gale et al. |
| 2006/0276345 A1 | 12/2006 | Todd et al. |
| 2006/0292198 A1 | 12/2006 | Dalal et al. |
| 2007/0003592 A1 | 1/2007 | Hissink |
| 2007/0009465 A1 | 1/2007 | Lendlein et al. |
| 2007/0009606 A1 | 1/2007 | Serdy et al. |
| 2007/0010831 A1 | 1/2007 | Romero-Ortega et al. |
| 2007/0020469 A1 | 1/2007 | Wood et al. |
| 2007/0027554 A1 | 2/2007 | Biran et al. |
| 2007/0032857 A1 | 2/2007 | Schmid |
| 2007/0034615 A1 | 2/2007 | Kleine |
| 2007/0043426 A1 | 2/2007 | Abbate |
| 2007/0055364 A1 | 3/2007 | Hossainy et al. |
| 2007/0071879 A1 | 3/2007 | Rypacek et al. |
| 2007/0071926 A1 | 3/2007 | Rypacek et al. |
| 2007/0087033 A1 | 4/2007 | Sigg et al. |
| 2007/0101578 A1 | 5/2007 | Shirazi |
| 2007/0114211 A1 | 5/2007 | Reynolds et al. |
| 2007/0116739 A1 | 5/2007 | Calhoun et al. |
| 2007/0117959 A1 | 5/2007 | Shastri et al. |
| 2007/0123977 A1 | 5/2007 | Cottone, Jr. et al. |
| 2007/0128723 A1 | 6/2007 | Cottone, Jr. et al. |
| 2007/0129789 A1 | 6/2007 | Cottone, Jr. et al. |
| 2007/0134305 A1 | 6/2007 | Zilberman |
| 2007/0135578 A1 | 6/2007 | Mather |
| 2007/0141107 A1 | 6/2007 | Kutryk et al. |
| 2007/0149640 A1 | 6/2007 | Andjelic et al. |
| 2007/0149724 A1 | 6/2007 | Pacetti et al. |
| 2007/0151961 A1 | 7/2007 | Kleine et al. |
| 2007/0155943 A1 | 7/2007 | Yang et al. |
| 2007/0191963 A1 | 8/2007 | Winterbottom et al. |
| 2007/0198040 A1 | 8/2007 | Buevich et al. |
| 2007/0202148 A1 | 8/2007 | Ringeisen et al. |
| 2007/0224245 A1 | 9/2007 | Ameer et al. |
| 2007/0231362 A1 | 10/2007 | Perez et al. |
| 2007/0231365 A1 | 10/2007 | Wang et al. |
| 2007/0233232 A1 | 10/2007 | St. Germain |
| 2007/0238167 A1 | 10/2007 | Perez et al. |
| 2007/0253996 A1 | 11/2007 | Bin et al. |
| 2007/0254012 A1 | 11/2007 | Ludwig et al. |
| 2007/0270941 A1 | 11/2007 | Headley et al. |
| 2007/0275020 A1 | 11/2007 | Lendlein et al. |
| 2007/0282425 A1 | 12/2007 | Kleine et al. |

(56) References Cited

U.S. PATENT DOCUMENTS

2008/0051866 A1  2/2008  Chen
2008/0118546 A1  5/2008  Thatcher
2008/0247987 A1  10/2008 Liggins et al.

FOREIGN PATENT DOCUMENTS

| | | |
|---|---|---|
| EP | 0709420 A2 | 5/1996 |
| EP | 0809981 A1 | 12/1997 |
| EP | 0999227 A2 | 5/2000 |
| EP | 1064958 A1 | 1/2001 |
| EP | 1138336 A1 | 10/2001 |
| EP | 1334990 A1 | 8/2003 |
| EP | 1374921 A1 | 1/2004 |
| EP | 1375557 A1 | 1/2004 |
| EP | 1382628 A1 | 1/2004 |
| EP | 1452191 A2 | 9/2004 |
| EP | 1462131 A1 | 9/2004 |
| EP | 1695718 A2 | 8/2006 |
| EP | 1728811 A1 | 12/2006 |
| EP | 1764118 A2 | 3/2007 |
| WO | WO 9003768 A1 | 4/1990 |
| WO | WO 9116368 A1 | 10/1991 |
| WO | WO 9204393 A1 | 3/1992 |
| WO | WO 9215340 A1 | 9/1992 |
| WO | WO 9309765 A1 | 5/1993 |
| WO | WO 9526762 A1 | 10/1995 |
| WO | WO 9619519 A1 | 6/1996 |
| WO | WO 9705193 A1 | 2/1997 |
| WO | WO 9711724 A1 | 4/1997 |
| WO | WO 9715287 A1 | 5/1997 |
| WO | WO 9715389 A1 | 5/1997 |
| WO | WO 9902201 A1 | 1/1999 |
| WO | WO 9910403 A1 | 3/1999 |
| WO | WO 9910404 A1 | 3/1999 |
| WO | 99/34750 A1 | 7/1999 |
| WO | WO 0113819 A2 | 3/2001 |
| WO | WO 0142333 A2 | 6/2001 |
| WO | WO 0185224 A1 | 11/2001 |
| WO | WO 0207749 A2 | 1/2002 |
| WO | WO 0231037 A1 | 4/2002 |
| WO | WO 0245685 A2 | 6/2002 |
| WO | WO 02092691 A1 | 11/2002 |
| WO | WO 03000766 A1 | 1/2003 |
| WO | WO 03020330 A2 | 3/2003 |
| WO | WO 03033042 A1 | 4/2003 |
| WO | WO 03034940 A2 | 5/2003 |
| WO | WO 03051328 A1 | 6/2003 |
| WO | WO 03055469 A1 | 7/2003 |
| WO | WO 03066705 A1 | 8/2003 |
| WO | WO 03068289 A1 | 8/2003 |
| WO | WO 2004028269 A1 | 4/2004 |
| WO | WO 2004028583 A2 | 4/2004 |
| WO | WO 2004045653 A2 | 6/2004 |
| WO | WO 2004053112 A1 | 6/2004 |
| WO | WO 2004069918 A2 | 8/2004 |
| WO | WO 2004080332 A2 | 9/2004 |
| WO | WO 2004091435 A2 | 10/2004 |
| WO | WO 2004108180 A1 | 12/2004 |
| WO | WO 2004110315 A1 | 12/2004 |
| WO | WO 2004112854 A1 | 12/2004 |
| WO | WO 2005002596 A1 | 1/2005 |
| WO | WO 2005013891 A2 | 2/2005 |
| WO | WO 2005027988 A2 | 3/2005 |
| WO | WO 2005039489 A2 | 5/2005 |
| WO | WO 2005041811 A2 | 5/2005 |
| WO | WO 2005051316 A2 | 6/2005 |
| WO | WO 2005051445 A1 | 6/2005 |
| WO | WO 2005051452 A2 | 6/2005 |
| WO | WO 2005061617 A1 | 7/2005 |
| WO | WO 2005065079 A2 | 7/2005 |
| WO | WO 2005074913 A2 | 8/2005 |
| WO | WO 2005110437 A2 | 11/2005 |
| WO | WO 2005114323 A2 | 12/2005 |
| WO | WO 2005117836 A2 | 12/2005 |
| WO | WO 2005123155 A2 | 12/2005 |
| WO | WO 2006002381 A1 | 1/2006 |
| WO | WO 2006020922 A2 | 2/2006 |
| WO | WO 2006020994 A2 | 2/2006 |
| WO | WO 2006023672 A2 | 3/2006 |
| WO | WO 2006026325 A2 | 3/2006 |
| WO | WO 2006044890 A2 | 4/2006 |
| WO | WO 2006053836 A1 | 5/2006 |
| WO | WO 2006060235 A2 | 6/2006 |
| WO | WO 2006066572 A2 | 6/2006 |
| WO | WO 2006066575 A1 | 6/2006 |
| WO | WO 2006069010 A2 | 6/2006 |
| WO | WO 2006071520 A2 | 7/2006 |
| WO | WO 2006073631 A1 | 7/2006 |
| WO | WO 2006074391 A2 | 7/2006 |
| WO | WO 2006074406 A2 | 7/2006 |
| WO | WO 2006078356 A1 | 7/2006 |
| WO | WO 2006111578 A1 | 10/2006 |
| WO | WO 2006128704 A1 | 12/2006 |
| WO | WO 2006130440 A1 | 12/2006 |
| WO | WO 2006135479 A2 | 12/2006 |
| WO | WO 2007019439 A2 | 2/2007 |
| WO | WO 2007041593 A2 | 4/2007 |
| WO | WO 2007041972 A1 | 4/2007 |
| WO | WO 2007059253 A2 | 5/2007 |
| WO | WO 2007084609 A2 | 7/2007 |
| WO | WO 2007085702 A1 | 8/2007 |
| WO | WO 2007092559 A2 | 8/2007 |
| WO | WO 2007115018 A2 | 10/2007 |
| WO | WO 2007115245 A2 | 10/2007 |
| WO | WO 2007117222 A1 | 10/2007 |
| WO | WO 2007117499 A2 | 10/2007 |
| WO | WO 2007126598 A2 | 11/2007 |
| WO | WO 2007126599 A2 | 11/2007 |
| WO | WO 2007132294 A2 | 11/2007 |
| WO | WO 2007132295 A2 | 11/2007 |
| WO | WO 2007136576 A2 | 11/2007 |
| WO | WO 2007140325 A2 | 12/2007 |
| WO | WO 2007140964 A2 | 12/2007 |
| WO | WO 2007143063 A2 | 12/2007 |
| WO | WO 2007143116 A2 | 12/2007 |
| WO | WO 2008011175 A2 | 1/2008 |
| WO | WO 2008089434 A2 | 7/2008 |

OTHER PUBLICATIONS

"International Preliminary Report on Patentability", Patent Cooperation Treaty completion date Sep. 15, 2010, PCT/US2007/082033 (filed Oct. 20, 2007), 6 pgs.

"International Search Report", International Searching Authority mailed May 15, 2009, PCT/US10/035169 (filed May 17, 2010), 3 pgs.

"International Search Report", International Searching Authority mailed Mar. 26, 2008, PCT/US2007/074054 (filed Jul. 20, 2007), 2 pgs.

"International Search Report", Korean Intellectual Property Office mailed Apr. 16, 2008, PCT/US2007/082033 (filed Oct. 20, 2007), 2 pgs.

"International Search Report", Korean Intellectual Property Office mailed Jun. 17, 2008, PCT/US2007/082034 (filed Oct. 20, 2007), 3 pgs.

"PolyLactic Acid", wikipedia.com, accessed Mar. 12, 2012, 6 pgs.

"Polymer Chemistry: The Glass Transition", University of South Carolina Upstate. 1-3. http://faculty.uscupstate.edu/ llever/ Polymer%20Resources/GlassTrans.htm (last updated Jul. 11, 2000).

"Supplementary European Search Report", European Patent Office dated Aug. 23, 2012, EP Application No. 07871194.2 (filed Oct. 20, 2007), 6 pgs.

"Supplementary European Search Report", European Patent Office dated Oct. 29, 2012, EP Application No. 07854261.0 (filed Oct. 20, 2007), 6 pgs.

"Supplementary European Search Report", European Patent Office dated May 30, 2014, EP Application No. 10775683.5 (filed May 17, 2010), 6 pgs.

"The Glass Transition", Penn State University, 1-30, http://www.personal.psu.edu/irh1/PDF/Glass%20Temperature.pdf (last visited Sep. 26, 2012).

(56) References Cited

OTHER PUBLICATIONS

"Written Opinion of the International Searching Authority", International Searching Authority mailed Mar. 26, 2008, PCT/US2007/074054 (filed Jul. 20, 2007), 3 pgs.
"Written Opinion of the International Searching Authority", Korean Intellectual Property Office mailed Apr. 16, 2008, PCT/US2007/082033 (filed Oct. 20, 2007), 5 pgs.
"Written Opinion of the International Searching Authority", Korean Intellectual Property Office mailed Jun. 17, 2008, PCT/US2007/082034 (filed Oct. 20, 2007), 6 pgs.
Finet; et al., "Coronary stent longitudinal deformation by compression: is this a new global stent failure, a specific failure of a particular stent design or simply an angiographic detection of an exceptional PCI complication?", EuroIntervention (Jun. 2012), 8(2):177-81.
Office Action dated Aug. 12, 2014, The State Intellectual Property Office of the People's Republic of China, Chinese Application No. 201310025670.4 (filed Jul. 20, 2007), 15 pgs.
The Matyjaszewski Polymer Group, "Molecular Assembly of Block Copolymers", Carnegie Mellon University, 1-4, http://www.cmu.edu/maty/materials/Properties-of-well-defined/molecular-assembly-of-block-copolymers.html (last visited Sep. 26, 2012).
Tsuji, "Poly(lactide) stereocomplexes: formation, structure, properties, degradation, and applications", Macromol Biosci (Jul. 2005), 5(7):569-97.
Wholey; et al., "Designing the Ideal Stent", Endovascular Today (Mar. 2007), pp. 25-34.
Zhang; et al., "Preparation of linear low-density polyethylene by the in situ copolymerization of ethylene with an iron oligomerization catalyst and rac-ethylene bis(indenyl) zirconium (IV) dichloride", Journal of Polymer Science Part A: Polymer Chemistry (Mar. 2005), 43(5):984-993.
Amecke; et al., "Resorbable Polyesters: Composition, Properties, Applications", Clinical Materials (1992), 10:47-50.
Baimark; et al., "Synthesis and characterization of poly(L-lactideco-e-caprolactone) (B)-poly(L-lactide) (A) ABA block copolymers", Polym. Adv. Technol. (2005), 16:332-337.
Baimark; et al., "Synthesis, characterization and melt spinning of a block copolymer of L-lactide and ε-caprolactone for potential use as an absorbable monofilament surgical suture", Journal of Materials Science: Materials in Medicine (2005), 16:699-707.
Bigg, "Polylactide Copolymers: Effect of Copolymer Ratio and End Capping on Their Properties", Advances in Polymer Technology (2005), 24(2):69-82.
Broz; et al., "Structure and mechanical properties of poly(d,l-lactic acid)/poly(e-caprolactone) blends", Biomaterials (2003), 24:4181-4190.
Cohn; et al., "Designing biodegradable multiblock PCL/PLA thermoplastic elastomers", Biomaterials (2005), 26:2297-2305.
Dell'Erba; et al., "Immiscible polymer blends of semicrystalline biocompatible components: thermal properties and phase morphology analysis of PLLA/PCL blends", Polymer (2001), 42:7831-7840.
Feng; et al., "Synthesis and evaluation of biodegradable block copolymers of ε-caprolactone and DL-lactide", Journal of Polymer Science: Polymer Letters Edition (1983), 21(8):593-600.
Feng; et al., "Synthesis and drug controlled release of block copolymers of poly(L-lactide) with poly(D,L-lactide) and related monomers", Macromol. Symp. (1997), 118:625-630.
Ge; et al., "Preparation, Characterization, and Drug Release Behaviors of Drug-Loaded ε-Caprolactone/L-lactide Copolymer Nanoparticles", Journal of Applied Polymer Science (2000), 75:874-882.
Goffin; et al., "New organic—inorganic nanohybrids via ring opening polymerization of (di)lactones initiated by functionalized polyhedral oligomeric silsesquioxane", European Polymer Journal (2007), 43:4103-4113.
Grijpmaa; et al., "(Co)polymers of L-lactide, 1: Synthesis, thermal properties and hydrolytic degradation", Macromol. Chem. Phys. (1994), 195:1633-1647.
Hamley; et al., "Crystallization in Poly(L-lactide)-b-poly(-caprolactone) Double Crystalline Diblock Copolymers: A Study Using X-ray Scattering, Differential Scanning Calorimetry, and Polarized Optical Microscopy", Macromolecules (2005), 38:463-472.
Hamley; et al., "Melt Structure and its Transformation by Sequential Crystallization of the Two Blocks within Poly(L-lactide)-block-Poly(ε-caprolactone) Double Crystalline Diblock Copolymers", Macromol. Chem. Phys. (2006), 207:941-953.
Ho; et al., "Crystallization-Induced Orientation for Microstructures of Poly(L-lactide)-b-poly(-caprolactone) Diblock Copolymers", Macromolecules (2003), 36:9085-9092.
Kim; et al., "Effect of P(LLA-co-εCL) on the Compatibility and Crystallization Behavior of PCL/PLLA Blends", Journal of Applied Polymer Science (2000), 77:226-231.
Kim; et al., Synthesis and crystallization behavior of poly(L-lactide)-block(ε-caprolactone) copolymer, Polymer (2001), 42:7429-7441.
Kuriyama; et al., "Compatibility and biodegradation of poly(lactic acid)-polycaprolactone blend systems", Nippon Setchaku Gakkai (2000), 38:173-176.
Lee; et al., "Surface Structure and Stereocomplex Formation of Enantiomeric Polylactide Blends Using Poly(dimethyl siloxane) as a Probe Polymer", Macromol. Symp. (2006), 239:91-96.
Li; et al., "Synthesis of tadpole-shaped copolyesters based on living macrocyclic poly(ε-caprolactone)", Polymer (2006), 47(26):8406-8413.
Lim; et al., "Stereocomplex Formation between Enantiomeric PLA-PEG-PLA Triblock Copolymers: Characterization and Use as Protein-Delivery Microparticulate Carriers", Journal of Applied Polymer Science (2000), 75:1615-1623.
Lu; et al., "Shape memory effects of poly(L-lactide) and its copolymer with poly(ε-caprolactone)", Polymer Bulletin (2007), 58:381-391.
Lostocco; et al., "The effects of primary structure on the degradation of poly(ε-caprolactone)/poly(L-lactide) block copolymers", Polymer Degradation and Stability (1998), 59:303-307.
Lostocco; et al., "The Synthesis and Characterization of Polyesters Derived From L-Lactide and Variably-Sized Poly(Caprolactone)", Polymer Modification (1997), 45-57.
Lu; et al., "Structure and shape memory effects of poly(L-lactide) and its copolymers", Physica Scripta (2007), T129:231-235.
Lu; et al., "Shape memory property of poly(l-lactide-co--caprolactone) copolymers", Materials Science and Engineering A (2006), 438-440:857-861.
Maglio; et al., "Thermal properties of di- and triblock copolymers of poly(L-lactide) with poly(oxyethylene) or poly(ε-caprolactone)", Polymer (2003), 44:369-375.
Maglio; et al., "Immiscible Poly(L-lactide)/Poly(ε-caprolactone) Blends: Influence of the Addition of a Poly(L-lactide)-Poly(oxyethylene) Block Copolymer on Thermal Behavior and Morphology", Macromol. Chem. Phys. (2004), 205:946-950.
Na; et al., "Compatibilization Effect of Poly(ε-caprolactone)-b-poly(ethylene glycol) Block Copolymers and Phase Morphology Analysis in Immiscible Poly(lactide)/Poly(ε-caprolactone) Blends", Biomacromolecules (2002), 3:1179-1186.
Nalampang; et al., "Synthesis and characterization of poly(L-lactide-co-ε-caprolactone) copolymers: influence of sequential monomer addition on chain microstructure", Polym. Adv. Technol. (2007), 18:240-248.
Niamsa; Synthesis and Characterization of Poly(L-lactide-co-ε-caprolactone)-b-Poly(L-lactide) Biodegradable Diblock Copolyesters: Effect of the Block Lengths on Their Thermal Properties, Journal of Applied Polymer Science (2007), 106:3315-3320.
Pensec; et al., "Stereocomplex formation in enantiomeric diblock and triblock copolymers of poly (ε-caprolactone) and polylactide", Polymer Bulletin (2000), 45:373-380.
Piao; et al., "Synthesis and Characterization of Poly(ε-caprolactone)-Poly(L-lactide) Diblock Copolymers with an Organic Amino Calcium Catalyst", Journal of Applied Science (2006), 102:2654-2660.
Portinha; et al., "Influence of Preparation Conditions on the Self-Assembly by Stereocomplexation of Polylactide Containing Diblock Copolymers", Macromolecules (2004), 37:3401-3406.
Portinha; et al., "Stable Dispersions of Highly Anisotropic Nanoparticles Formed by Cocrystallization of Enantiomeric Diblock Copolymers", Macromolecules (2007), 40:4037-4042.

(56) References Cited

OTHER PUBLICATIONS

Lopez-Rodriguez; et al., "Crystallization, Morphology, and Mechanical Behavior of Polylactide/Poly(ε-caprolactone) Blends", Polymer Engineering and Science (2006), 1299-1308.

Slivniak; et al., "Stereocomplexes of Enantiomeric Lactic Acid and Sebacic Acid Ester-Anhydride Triblock Copolymers", Biomacromolecules (2002), 3:754-760.

Stevels; et al., "Well defined block copolymers of ε-caprolactone and L-lactide using Y5(μ-O)(O$^i$Pr)13a) as an initiator", Macromol. Chem. Phys. (1995), 196:1153-1161.

Stevels; et al., "Stereocomplex formulation in ABA triblock copolymers of poly(lactide) (A) and poly(ethylene glycol) (B)", Macromol. Chem. Phys. (1995), 196:3687-3694.

Stevels; et al., "Stereocomplex Formation in AB Di-Block Copolymers of Poly(ε-Caprolactone) (A) and Poly(Lactide) (B)".

Tamura; et al., "Synthesis of Poly(Methylacrylate-b-ε-Caprolactone) and Application to Compatibilizer for Poly(L-Lactide)/Poly(ε-Caprolactone) Blend System", Materials Transactions (2005), 46(12):2668-2672.

Teng; et al., "Synthesis and Characterization of Poly(L-lactic acid)-Poly(ε-caprolactone) Multiblock Copolymers by Melt Polycondensation", Journal of Polymer Science: Part A: Polymer Chemistry (2004), 42:5045-5053.

Tsuji; et al., "Enhanced Crystallization of Poly(L-lactide-co-ε-caprolactone) During Storage at Room Temperature", Journal of Applied Polymer Science (2000), 76:947-953.

Tsuji; et al., "Blends of aliphatic polyesters. Part 7. Effects of poly(L-lactide-co-ε-caprolactone) on morphology, structure, crystallization, and physical properties of blends of poly(L-lactide) and poly(ε-caprolactone)", Polymer International (2003), 52:269-275.

Tsuji; et al., "Melt-Processed Biodegradable Polyester Blends of Poly(L-lactic acid) and Poly(ε-caprolactone): Effects of Processing Conditions on Biodegradation", Journal of Applied Polymer Science (2007), 104:831-841.

Tsuji; et al., "Porous biodegradable polyester blends of poly(L-lactic acid) and poly(ε-caprolactone): physical properties, morphology, and biodegradation", Polymer International (2007), 56:258-266.

Wang; et al., "Synthesis, Sequential Crystallization and Morphological Evolution of Well-Defined Star-Shaped Poly(ε-caprolactone)-b-poly(L-lactide) Block Copolymers", Macromol. Chem. Phys. (2006), 207:554-562.

Wei; et al., "Melting and Crystallization Behaviors of Biodegradable Polymers Enzymatically Coalesced from Their Cyclodextrin Inclusion Complexes", Biomacromolecules (2003), 4:783-792.

Xu; et al., "Improvements of thermal property and crystallization behavior of PLLA based multiblock copolymer by forming stereocomplex with PDLA oligomer", Polymer (2006), 47:3922-3928.

Yang; et al., "Miscibility and Crystallization of Poly(L-lactide)/Poly-(ethylene glycol) and Poly(L-lactide)/Poly(ε-caprolactone) Blends", Polymer Journal (1997) 29(8):657-662.

Yavuz; et al., "Preparation and degradation of l-lactide and ε-caprolactone homo and copolymer films", Polymer Degradation and Stability (2002), 75:431-437.

Zhang; et al., "Synthesis and Characterization of Dendritic Star-Shaped Poly(e-caprolactone)-block-Poly(L-lactide) Block Copolymers", Journal of Applied Polymer Science (2007), 106:417-424.

* cited by examiner

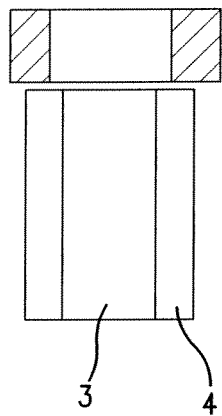 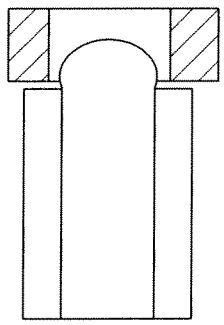 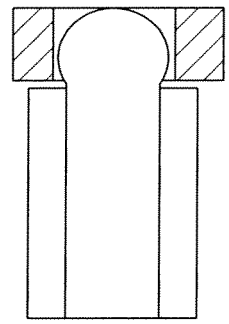 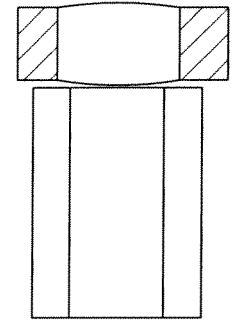
FIG. 3A  FIG. 3B  FIG. 3C  FIG. 3D
 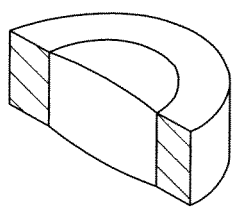 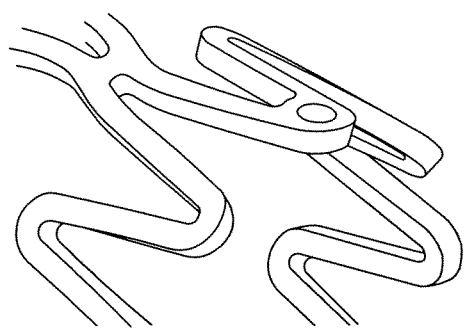
FIG. 3E  FIG. 3F  FIG. 3G

A-1-1

A-1-2

BIOABSORBABLE POLYMERIC COMPOSITION FOR A MEDICAL DEVICE

CROSS-REFERENCE TO RELATED APPLICATIONS

This application is a continuation application of U.S. patent application Ser. No. 12/508,442, filed on Jul. 23, 2009, which is a divisional application of U.S. patent application Ser. No. 11/781,230, filed on Jul. 20, 2007, now U.S. Pat. No. 7,846,361, which claims benefit of U.S. Provisional Application Nos. 60/807,932, filed on Jul. 20, 2006; and 60/862,433, filed on Oct. 20, 2006.

All references cited in this specification, and their references, are incorporated by reference herein in their entirety where appropriate for teachings of additional or alternative details, features, and/or technical background.

FIELD OF INVENTION

Disclosed in the embodiments herein is a novel polymer composition, which includes a base material including a one or more bioabsorbable polymer, copolymer, or terpolymer, with a polymer or copolymer or terpolymer additive. In particular, the novel composition when used to fabricate implants allows for a "soft" breakdown mechanism allowing for the breakdown of the component polymers to be less injurious to the surrounding tissue.

BACKGROUND OF INVENTION

A persistent problem associated with the use of metallic stenting is found in the formation of scar tissue coating of the vascularly located stent, the so-called process of restenosis. Moreover, metallic or polymeric non-absorbable stents may prevent vascular lumen remodeling and expansion. Numerous approaches have been tried to prevent or heal tissue injury and reduce complement activation of the immune response. Furthermore, there is a need for a reduced inflammatory response and lower potential for trauma upon break-up of an implant and/or its component materials. A desirable improvement target may be found in the need for increased flexibility of shape and structure of medical devices for implantation, particularly into blood vessels.

Among the many commercially available bioabsorbable polymers are poly-alpha-esters (e.g., lactides (i.e., L-lactide and D,L-lactide)) and glycolides, polyester ethers (i.e. polydioxanone), and polycarbonates (i.e., glycolide or lactide-co-trimethylene carbonate), and tyrosine based polycarbonates. Many other bioabsorbable polymers are being developed for commercial use, particularly in different modes of drug delivery, which polymeric substances include polyethylene glycol-co-lactides, polyanhydrides, polyorthoesters, polyesteramides or cyanoacrylates.

The present inventors have recognized a need to develop a compatible polymer blend for implants, such as stents and vascular synthetic grafts, which provide a toughening mechanism to the base polymer when the medical device is deployed in the body. They have hypothesized that the later may be performed by imparting additional molecular free volume to the base polymer to encourage sufficient molecular motion to allow for re-crystallization to occur at physiological conditions especially when additional molecular strain is imparted to the implant. They have theorized that increased molecular free volume can also increase the rate of water uptake adding both a plasticizing effect as well as increasing the bulk degradation kinetics.

REFERENCES

Reference is made to U.S. Pat. No. 6,607,548 B2 (Inion Ltd), issued Aug. 19, 2003, which discloses compositions are biocompatible and bioresorbable using a lactic acid or glycolic acid based polymer or copolymer blended with one or more copolymer additives. Implants made according to the '548 disclosure are said to be cold-bendable without crazing or cracking. Reference is also made to EP 0401844 which discloses a blend of poly-L-lactide with poly L-DL-lactide. Reference is also made to U.S. Pat. No. 5,317,064 disclosing polylactide stereocomplexing compositions.

SUMMARY

A novel polymer composition is provided that allows for a "soft" breakdown in vivo such that the breakdown proceeds while being friendly to the surrounding tissue (e.g., less inflammatory response, and rendering lower potential for trauma upon break-up of an implant). The polymer composition includes a base material such as a bioabsorbable polymer, copolymer, or terpolymer, which are selected for their ability to undergo hydrolytic and/or enzymatic degradation and absorption in vivo, and a copolymer or terpolymer additive.

Such novel polymer composition may comprise a polymer blend with the blend being optimized for enhanced hydrophilic property in order to reduce complement activation and minimize or prevent opsonization (see Dong and Feng, J of Biomedical Materials Research part A DOI 10.1002, 2006). To improve hydrophilicity, the novel polymer composition may be formulated to provide increased molecular free volume, allowing for increased uptake of water, and the rate of uptake of water, adding both a plasticizing effect as well as increasing the bulk degradation kinetics. Additional molecular free volume may also be used to encourage sufficient molecular motion so as to allow for re-crystallization to occur at physiological conditions, in particular when strain on the composition leads to additional molecular strain.

In an embodiment, there is provided a polymer/polymer blend implant comprising a biodegradable scaffold displaying flexibility for crimped fastening on a carrier system, as well as displaying elastic strut strength upon implantation into the body due to induction of crystallization if the polymer/polymer blend. The implant may comprise, for example, a tube-shaped expandable scaffold configured to fit within an organ space, such as the vasculature, including the cardiovasculatory system. Such a scaffold may achieve a combination of mechanical properties balancing elasticity, rigidity and flexibility.

In one embodiment the polymer composition and/or formulation, contains a polymer such as a poly(L-lactide), and/or a poly(D-lactide) as the base polymer, or copolymers thereof. In respect of copolymer compositions, the copolymers may be synthesized as block copolymers or as "blocky" random copolymers. The lactide chain length of copolymers may be selected to be sufficiently long enough to crystallize. Shortened degradation time, to provide, for example, enhanced degradation kinetics may be obtained by using a lower molecular weight composition and/or a base polymer that is more hydrophilic or suspect to hydrolytic chain scission.

Optionally included in such embodiment composition is modifying copolymers including, for example, poly L (or D)-lactide-co-tri-methylene-carbonate, or poly L (or D)-lactide-co-ϵ-caprolactone, which may be admixed to link the base polymers. In such copolymer-modifying copolymer embodiment, the composition may allow the development of a crystal morphology that can enhance the mechanical properties of the medical device, enhance processing conditions, and provide potential of cross-moiety crystallization, for example, strain induced thermal cross-links. The modifying polymer or co-polymer may also be used to affect enhanced degradation kinetics, such as with an ε-caprolactone copolymer moiety where the caprolactone remains amorphous with resulting segments more susceptible to hydrolysis.

In another embodiment composition the base copolymer includes L-lactide/D-lactide wherein one chain moiety is sufficiently long enough, and not sterically hindered, to crystallize with another lactide moiety. Optional co-moners with the base co-polymer include lesser sized moieties such as, for example, glycolide, polyethylene glycol (PEG), or monomethoxy-terminated PEG (PEG-MME).

In another embodiment, one may incorporate PEG copolymers, for example either AB di-block or ABA tri-block with the PEG moiety being approximately 1%, may be employed with maintenance of the mechanical properties of the lactide (see Enderlie and Buchholz S F B May 2006). Incorporation of either PEG or PEG-MME copolymers may also be used to facilitate drug attachment to the polymer, for example, in conjunction with a drug eluting medical device.

Embodiment hydrophilic compositions of the present invention are intended to allow for a "soft" or very gradual breakdown mechanism such that the breakdown proceeds while being friendly to the surrounding tissue (less inflammatory response, and rendering lower potential for trauma upon break up of an implant). Selecting a polymer or copolymer having an enhanced hydrophilic property for either the base polymer, or the additive, or both, the polymer blend may reduce complement activation and minimize or prevent opsonization.

In an embodiment composition, the polymers are selected to provide a racemate or stereocomplex crystal structure. For example, the copolymers may comprise a D-lactide and L-lactide, in a ratio sufficient to form a racemic crystal structure. A scaffold produced of such polymer compositions may provide enhanced mechanical properties through a molecular reorientation and crystallization effected during the radial strain of expansion from a crimped state to an expanded or implanted state. More specifically, a tubular stent scaffold of such embodiment may undergo racemate crystallization at the more tightly angled meandering struts after being crimped on to a carrier/implanting device, while still maintaining a substantially amorphous matrix elsewhere. When a tubular stem scaffold includes a hoop structure, the polymer may be fabricated so as to be capable of crystallization in the orthogonally expansion stretched ring or hoop structures during implantation generating strong resistance against collapse.

In another embodiment, cross-moiety crystallization is promoted between a base polyer, e.g., poly L-lactide or poly D-lactide, and a modifying copolymer with the same lactide segment, e.g., LPLA-TMC or DPLA-TMC respectively.

The composition of the polymer embodiments also may be modified for the particular functions assigned to a medical device. Thus, the polymer may contain fillers in the form of drugs or other pharmaceutical agents such as small molecule inhibitors of endogenous enzymes, radio-opaque markers (powders or other suitable particulates, and other factors.

The compositions of the present invention may include pharmacological agents such as tacrolimus, sirolimus, everolimus, prostacyclin, prostacyclin analogs, α-CGRP, α-CGRP analogs or α-CORP receptor agonists; prazosin; monocyte chemoattractant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like.

Included in embodiments of the present invention are devices made from such polymer compositions. Such devices include medical devices for implantation into a patient such as, without limitation, biodegradable, stents, stent grafts, vascular synthetic grafts, orthopedic devices, nerve guides, maxillofacial cranial devices, catheters, vascular shunts, or valves. Such devices may display bioabsorbable properties. Such implantation devices may include structure useful for inserting the implant into the body. For example, such implants may include snap-fit structure allowing for interaction between suitable parts of the medical device to allow the device to be held in a reduced size state which may aid in its insertion, and may aid its interaction with a carrier device used for its insertion (e.g., securing it on a carrier device without creep).

Embodiments of the invention are also directed to methods of making the biodegradable polymer compositions and methods for making the medical devices from the polymer compositions disclosed herein.

BRIEF DESCRIPTION OF THE DRAWINGS

FIGS. 3A-3G illustrate an embodiment method of radiopaque depot marking of a stent medical device: as seen in (a)-(d)) radiopaque material may be extruded into a cavity housed in the structure (g). As seen in cut-off views (e) and (f), such cavity may be a through-hole.

As illustrated in FIGS. 5A and 5B the radiopaque markers can be aligned in the structure to allow for easier identification upon imaging or use of other detection methods.

DETAILED DESCRIPTION

Figure 1:
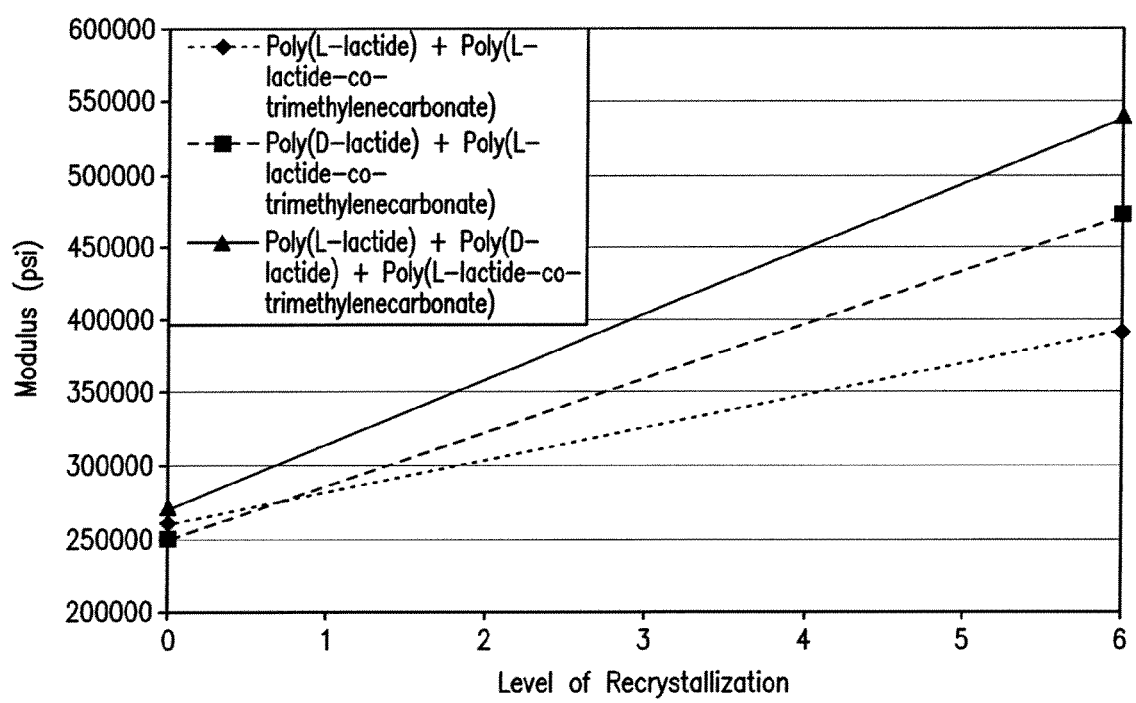
FIG. 1 depicts change in modulus with recrystallization of LPLA/LPLA/TMC non-racemate blend versus a DPLA/LPA/TMC with only cross moiety racemate and a DPLA/LPLA/LPLA-TMC with additional racemate formation.

In embodiments herein there are illustrated various compositions for bioabsorbable polymer blends, methods for making the compositions, and medical devices made of such bioabsorbable polymer blends.

The following nomenclature will now be used with the polymer nomenclature being based on the presence of the monomer type.

LPLA: Poly(L-lactide)
LPLA-PEG: Poly(poly-L-lactide-polyethylene glycol)
DPLA: Poly(D-lactide)
DPLA-TMC: Poly(poly D-lactide-co-trimethylene carbonate)
DLPLA: Poly(DL-lactide), a racemic copolymer D-co-L-lactide
LDPLA: Poly(L-co-D-lactide)
LDLPLA: Poly(L-co-DL-lactide), named for the method of monomer introduction
PGA: Poly(glycolide)
PDO: Poly(dioxanone) (PDS is Trademark)
SR: "Self reinforced" (a processing technique)
TMC: Trimethylene carbonate
PCL: Poly($\epsilon$-caprolactone)
LPLA-TMC: Poly(poly L-lactide-co-trimethylene carbonate)
LPLG: Poly(L-lactide-co-glycolide)
POE: Poly Orthoester In an embodiment of the present invention, the composition comprises a base polymer of poly(L-lactide) or poly(D-lactide). Advantageous base polymer compositions include blends of poly(L-lactide) and poly(D-lactide). Other advantageous base polymer compositions include poly(L-lactide-co-D,L-lactide) or poly(D-lactide-co-D,L-lactide) with a D,L-lactide co-monomer molar ratio from 10 to 30%, and poly(L-lactide-co-glycolide) or poly(D-lactide-co-glycolide) with a glycolide co-monomer molar ratio from 10 to 20%.

Another embodiment embodies a base polymer featuring a poly(L-lactide) moiety, and/or a poly(D-lactide) moiety, linked with a modifying copolymer thereof, including poly(L-lactide-co-tri-methylene-carbonate or poly(D-lactide-co-tri-methylene-carbonate) and (L-lactide-co-$\epsilon$-caprolactone), or poly(D-lactide-co-$\epsilon$-caprolactone), in the form of block copolymers or blocky random copolymers, wherein the lactide chain length is sufficient to affect cross-moiety crystallization.

In another embodiment, the polymer composition allows the development of the lactide racemate (stereo complex) crystal structure, between the L and D moieties, to further enhance the mechanical properties of the bioabsorbable polymer medical device. The formation of the racemate (stereo complex) crystal structure can accrue from formulations such as combinations of:

Poly L-lactide with Poly D-lactide with Poly L-lactide-co-TMC;
Poly D-lactide with Poly L-lactide-co-TMC;
Poly L-lactide with Poly D-lactide-co-TMC;
Poly L-lactide with Poly D-lactide with Poly D-lactide-co-TMC;
Poly L-lactide-co-PEG with Poly D-lactide-co-TMC; and
Poly D-lactide-co-PEG with Poly L-lactide-co-TMC.

Poly-lactide racemate compositions of this embodiment may have an especially advantageous characteristic in being "cold formable or bendable" without adding heat. Cold-bendable scaffolds of the invention do not require heating to become flexible enough to be crimped onto a carrier device or accommodate irregularly shaped organ spaces. Cold bendable ambient temperatures are defined as room temperature not exceeding 30° C. Cold-bendable scaffolds, for example, afford sufficient flexibility when implanted allowing for an expanded scaffold device in an organ space such as pulsating vascular lumen. For example, in terms of a stent, it may be desirable to utilize polymeric compositions that afford mostly amorphous polymer moieties after fabrication that can crystallize particularly when the secondary nested or end-positioned meandering struts when the scaffold is strained by stretching upon balloon expansion for implantation. Such cold-bendable polymeric scaffold embodiments of are not brittle and do not have to be preheated to a flexible state prior to implantation onto a contoured surface space in the body. Cold-bendability allows these blends to be crimped at room temperature without crazing, and moreover, the blends can be expanded at physiological conditions without crazing.

Poly-lactide racemate compositions and non-racemate compositions of embodiments herein may be processed to have blocky moieties allowing cross moiety crystallization even with the addition of an impact modifier to the blend composition. Such a blend introduces the possibility to design device specific polymer compositions or blends by producing either single or double Tg's (glass melt transition points).

Poly-lactide racemate compositions may show significant improvement in re-crystallization capability over, for example, non-racemate PLDL-lactide blends. An advantageous racemate alignment of the different polylactide moieties can be achieved, for example, by blending a poly-D-lactide with the copolymer poly L-lactide-co-TMC capable of forming racemate crystal across the different polylactide stereomoieties, for example, without limitation, when stretched during expansion to the required emplacement diameter. This strain induced crystallization, without adverse crazing, results in an increase of the mechanical properties reflected also in a positive change of modulus data over the base of the base materials.

Cross moiety crystallization of compositions with copolymers appears to be limited to copolymer with monomer molar ratios ranging from about 90:10 through 50:50. In fact, at a molar ratio of 50:50, the polymer moieties sterically impeded crystallization whereas the greater ratios are much more suitable for cross moiety crystallization. On the basis of experimental induced crystallization, different blends with various concentrations of lactide copolymers such as TMC or $\epsilon$CL, to which an excess of poly(D-lactide) for racemate alignment with the L-lactide component has been added, the effective concentration of the copolymer in a racemate composition may be equal to, or less than, 40%. Thus, the thermal cross-links formed by cross moiety crystallization serves to reduce elongation or creep while maintaining the intended toughening mechanism. The advantageously strong racemate composition affords increased modulus data in tensile tests avoiding the method for reducing the tensile strength in the polymer blend.

An advantageous racemate composition embodiment provides a bioabsorbable polymer with minimal degradation in terms of high residual monomer level such that the contaminant monomeric residual fraction does not exceed about 0.5%, or preferably not in excess of about 0.3%. In embodiment concentration of monomeric contaminant of the polymer of the present invention is as low as about 0.2%.

Polymer compositions of embodiments described herein may comprise a base polymer present from about 70% to 95% by weight, or from about 70% to 80% by weight of the composition. For example, in one embodiment, the polymer formulation may comprise from about 70% by weight poly L-lactide (about 2.5 to 3 IV) with the poly L-lactide-co-TMC (70/30 mole/mole) (1.4 to 1.6 IV). In another embodiment, the polymer formulation may comprise 70% by weight triblock poly L-lactide-co-PEG (99/01 mole/mole) (2.5 to 3 IV) with the poly L-lactide-co-TMC (70/30 mole/mole) (1.4 to 1.6 IV). Furthermore, the polymer composition may comprise a formulation of about 70% by weight diblock poly L-lactide-co-PEG-MME (95/05 mole/mole) (2.5 to 3 IV) with poly L-lactide-co-TMC (70/30 mole/mole) (1.4 to 1.6 IV). Other embodiments provide formulations wherein ε-caprolactone is substituted in a composition for the aforementioned TMC. Similarly, an embodiment may provide formulations wherein PEG-MME may be substituted for PEG.

As is understood in this art, polymer compositions of the present invention can be customized to accommodate various requirements of the selected medical device. The requirements include mechanical strength, elasticity, flexibility, resilience, and rate of degradation under physiological and localized anatomical conditions. Additional effects of a specific composition concern solubility of metabolites, hydrophilicity and uptake of water and any release rates of matrix attached or enclosed pharmaceuticals.

The polymer implant utility can be evaluated by measuring mass loss, decrease in molecular weight, retention of mechanical properties, and/or tissue reaction. More critical for scaffold performance are hydrolytic stability, thermal transitions crystallinity and orientation. Other determinants negatively affecting scaffold performance include, but not exclusively, monomeric impurities, cyclic and acyclic oligomers, structural defects and aging.

The medical device fashioned from the polymer compositions above may be significantly amorphous post extrusion or molding. Such devices may be subjected to controlled re-crystallization to induce incremental amounts of crystallinity and mechanical strength enhancement. Further crystallization can be induced by strain introduction at the time of device deployment. Such incremental re-crystallization may be employed either on a device "blank" prior to secondary or final fabrication (such as by laser cutting) or post such secondary fabrication. Crystallization (and thus mechanical properties) can also be maximized by strain induction such as by "cold" drawing polymeric tubing, hollow fiber, sheet or film, or monofilament prior to further fabrication. Crystallinity has been observed to contribute a greater stiffness in the medical device. Therefore, the polymer composition and steric complex of the scaffold has both amorphous and paracrystalline moieties. The initially semicrystalline polymer portion can be manipulated by the action of stretching or expansion of a given device. Yet an adequate amount of amorphous polymeric character is desirable for flexibility and elasticity of the polymeric device. The usual monomer components include lactide, glycolide, caprolactone, dioxanone, and trimethylene carbonate.

In one embodiment, the medical device manufactured from such composition is a scaffold strut structure for implantation into the body, for example, a stent. These structures are to be crimpable so as to be tightened around and thereby fastened on a carrier device. Conversely, the same scaffold is expandable without stress crazing or cracking. The mechanical properties of a stent biodegradable scaffold implant requires strength, elasticity and flexibility to cope with the fluctuating pulse compression of the surrounding tissue without dislocation and injurious impact at the implantation site throughout the desirable gradual process of biological degradation and absorption of the scaffold struts. Therefore, these properties have to be build into the scaffold polymer content and structure in terms of certain criteria. The stent should have polymeric properties are amenable to expansion by means of a thermally enhanced or non-thermal balloon. The polymeric embodiment provides the ability to orient and/or crystallize in scaffold struts upon orthogonal strain of deployment, by e.g. balloon dilation. Thus, the crystallization effect provides improved mechanical properties such as hoop strength, as in compression resistance, elastic recoil, and polymer stability. The stent may also be constructed to allow relatively uniform exposure to local tissue or circulatory bioactive factors and enzymes perfusing and acting on the polymer structure during bioabsorption.

Advantageously, the rate of in situ breakdown kinetics of the polymeric matrix of an organ space implant, such as a cardiovascular stem, is sufficiently gradual to avoid tissue overload, inflammatory reactions or other more adverse consequences. In an embodiment, the scaffold is fabricated to survive at least one month.

As shown in the following examples, the comparative degree of amorphous and crystalline properties can be designed into the polymer. Thus, L-lactic polymers are found to yield a semicrystalline morphology, while the racemic poly(D,L-lactic) results in an amorphous polymer. A poly(L-glycolide) is semicrystalline. The following examples show a process for fabricating bioabsorbable scaffold PLDL-lactide blends.

Example 1

A test disk was injection molded from a composition of a racemic mixture of poly(L-lactide) and poly(D-lactide) with 15% by weight copolymer modifier of a 50:50 molar ratio poly(L-lactide-co-TMC). Injection cylinder temperatures were between 110° C. and 225° C. with a mold temperature of 50° F. to 82° F., to mold an amorphous disk. Injection pressure was set between 1300 and 1450 psi with a 50 second cycle time. It was found that an adequate degree of crystallinity could be produced in the polymer. DSC analysis confirmed the formation of both the conventional lactide crystal and the racemate crystal morphology.

Example 2

The polymer mixture is blend extruded into a narrow tube, and a scaffold form may be cut with a laser under a microscope to produce a cage-like mesh device of meandering struts connected to hoop-like rings positioned at one end and/or at the middle portion of the device. The resulting scaffold device includes a primary meandering scaffold forming a circumferential mesh structure containing a pattern of secondary meandering struts nested within the scaffold as well as at or near the ends of the scaffold. The second meandering struts may be shaped to form upon full implant expansion, a less sinusoidal or more straight hoop or ring shape than the first meandering struts, in orthogonal direction to the longitudinal axis of the tubal device. The expanded second meandering struts having smaller or shorter meandering loops or curves are stretched further during expansion. These struts may form thus hoops of greater crystallinity and therefore greater rigidity with elasticity so that the implant is resistant against creeping change or dislocation.

Example 3

The polymer compositions may be prepared from commercially available granular materials and copolymer additives. The dry components are weighed according to the desired weight ratio into a container rotating in a suitable for 30 minutes or until a homogenous mixture is obtained followed by further drying in vacuo at 60° C. for 8-12 hours or overnight. As described above, the thoroughly mixed components may be melt blended and injection molded into a pair of matching plates. The composition rendering polymer sheets exhibiting a suitable elasticity and an appearance of amorphous morphology or very low degree of crystallinity under a polarizing light source may be extruded with a back pressure of 40-50 bar under melting temperature of 120-160° C. while being homogenized with a 28 blade screw at 40-80 rpm The extruder melt blending and homogenization conditions of the material during metering phase of the process may include a screw speed of 60-100 rpm. The relatively mild injection molding process may use an exit temperature of 120° C.-150° C., at a velocity of 80-300 mm/s, a maximum injection pressure of 2500 bar, a pack pressure of 1000-2300 bar for 3 to 8 seconds, into mold kept at room temperature. The total cycle time may be one minute or less from injection to ejection from the mold plate.

Example 4

Dry polymer racemate mixture of poly(D-lactide) and poly(L-lactide-co-TMC) was blended at a weight ratio of 70:30 and processed with a single melt-extrusion step at 185-225° C. into a tube-shaped amorphous bioabsorbable racemate capable polymer blend. The instant method of melt-extrusion minimized polymer degradation due to excessive exposure to heat and shear. Subsequent testing showed effective induction of crystallization and development of the racemate crystal morphology. Such racemate copolymer hybrids have been found to confirm effective cross moiety crystallization. Moreover, racemate material can be created to have multiple transition temperatures indicating polymorphic and or pleomorphic structures. Thus, it has been found that the instant polymer scaffold was sufficiently flexible to be crimped onto a rubber bulb carrier, but for deployment in tissue the polymer moiety strength may be increased proportionally to expansion strain.

Example 5

Dry poly(L-lactide) with a racemic excess of poly(D-lactide) were blended with 30% by weight poly(L-lactide-co-TMC) under dry nitrogen, followed by melt blending and extrusion followed by rapid air quenching. Subsequent re-crystallization and testing confirmed significantly more racemate formation and increase in modulus over the formulation of example 4.

Synthesis is influenced by several distinct factors affecting the mechanical performance of the bioabsorbable polymer suitable for an implantable structure, such as monomer selection, initiator selection, polymerization conditions, and presence of additives or residuals. Furthermore, polymeric properties that determine the effectiveness of the implant include hydrophilicity, crystallinity, melt and glass transition temperatures, molecular weight, molecular weight distribution, end groups, sequence distribution i.e., random vs. blocky), presence of residual monomer or additives, and stability during conversion.

In one embodiment, pharmaceutical compositions may be incorporated within the polymers by, for example, grafting to the polymer active sites, or coating. An embodiment of the polymer according to the invention affords attachment or incorporation the biological healing factors or other drugs in the polymeric matrix or a polymer coating.

In another embodiment, the composition may be constructed to structurally enclose or attach to drugs in the polymeric matrix. The purpose of such additives may to provide, for example with respect to a stent, treatment of the cardiovascular system or in vascular site in contact with the medical device polymer. The kind of enclosure or attachment of drugs in the polymer may determine the rate of release form the device. For example, the drug or other additive may be bound in the polymer matrix by various known methods including but not limited to covalent bonds, non-polar bonds as well as an ester or similar bioreversible bonding means.

Embodiments of the bioabsorbable polymeric scaffold of an implantable configuration are known as useful for drug delivery. Therefore as described below, an extensive variety of compounds are possible agents to treat or modify the affected tissue at the locus of implantation as well as possibly further as e.g. in the entire cardiovascular system or other affected organs.

Examples of compounds or pharmaceutical compositions which can be incorporated in the matrix, and/or impregnated into the medical device include, but are not limited to tacrolimus, sirolimus, everoolimus, prostacyclin, prostacyclin analogs, α-CGRP, α-CGRP analogs or α-CGRP receptor agonists; prazosin; monocyte chemoattractant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; anti-inflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1

(SERP-1) and the like. The aforementioned compounds and pharmaceutical substances can be applied to the scaffold of the device alone or in combinations and/or mixtures thereof. Moreover, the polymer attached or enclosed drug material can be bound covalently or ionically to the polymeric moieties as well as entrapped physically in the polymeric matrix. Wherever suitable the drug may be present in the form ester-type cross-links, microparticles, or micelle clusters.

In one embodiment, a bioabsorbable implantable medical device be covered with a biodegradable and bioabsorbable coating containing one or more barrier layers where the polymer matrix contains one or more of the aforementioned pharmaceutical substances. In this embodiment, the barrier layer may comprise a suitable biodegradable material, including but not limited to, suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphacenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydixanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethyl-carbonates; cyanoacrylate; calcium phosphates; polyglycosaminoglycans; macro-molecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the polymeric scaffold on a device may have depends on the amount of therapeutic need as dictated by the therapy required by the patient. For example, the longer the treatment, the more therapeutic substance required over a period of time, the more barrier layers to provide the pharmaceutical substance in a timely manner.

In another embodiment, the additive in the polymer composition may be in the form of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α ligands, tissue plasminogen activator, statins such as atorvastatin, erythropoietin, darbepotin, serine proteinase-1 (SERP-1) and pravastatin, steroids, and/or antibiotics.

In another embodiment, there is provided a method for treating vascular disease such as restenosis and atherosclerosis, comprising administering a pharmaceutical substance locally to a patient in need of such substance. The method comprises implanting into a vessel or hollowed organ of a patient a medical device of the present invention with a coating, which coating comprises a pharmaceutical composition comprising a drug or substance for inhibiting or slowing smooth muscle cell migration and thereby restenosis, and a biocompatible, biodegradable, bioerodable, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

The medical devices which may be made from the compositions of the present disclosure may comprise any medical device for implantation including, without limitation, stents, grafts, stent grafts, synthetic vascular grafts, shunts, catheters, and the like. The medical device embodiments of the present invention may provide a drug delivery system that features different gradual release rates of a drug or a mixture of drugs for effective treatment of the implant site in a tissue or organ structure. Such devices may also include in the composition, or in the structure composed of the composition, radiopaque substances for enhancing traceability of the medical device in situ. Such radiopaque substances may include nontoxic materials which would interfere with the intended healing process.

The medical devices of the invention can be structurally configured to provide the ability to change and conform to the area of implantation to allow for the normal reestablishment of local tissues. The medical devices can transition from solid to a "rubbery state" allowing for easier surgical intervention, than, for example, a stainless steel stem. Moreover, the rubbery state of the device offers less risk of any injurious encounters with the vascular walls in the event of a removal from a vascular location.

In embodiments disclosed herein, the medical device comprises a stent, which is structurally configured to be deployed into, for example, an artery or a vein, and be able to expand in situ, and conform to the blood vessel lumen to reestablish blood vessel continuity at the site of injury. The stent can be configured to have many different arrangements so that it is crimpable when loading and expandable and flexible at physiological conditions once deployed. Various embodiments of biodegradable polymeric stents, and/or stent walls with different configuration may be envisioned, as are illustrated in co-pending patent applications. For example, the stent is a tubular structure comprising struts operably designed to allow blood to traverse its walls so that the adjacent tissues are bathed or come in contact with it as blood flows through the area. The particular stent design depends on the size of the stent radially and longitudinally.

In respect of stents, the composition of the polymer may be designed to afford a combination of rigidity, elasticity, and flexibility such that the in situ effect of the stent results in effective luminal support for healing and drug treatment of the cardio-vascular system. With respect to stents, in particular, the composition of the polymers may be adjusted and selected such that it affords sufficient polymer strength to resist fluctuating vascular compression forces and blood flow rates. This structural and flexural strength is designed to persist during in situ bio-erosion of polymeric material which may extend over many days, or a few months. This residual strength of the polymer can be measurably monitored for at least enough time before a collapse of the treated vessel and keep the healing process on track. A composition for a stent may be designed to provide transitions gradually from the initial rigidly buttressing character within a vascular location to a rubber-like or "rubbery" consistency capable of maintaining a clinical function, such as preventing restenosis. The polymer composition may further be selected to offer smooth polymerized surfaces both proximal and distal to vascularly engaged regions so as to minimize tissue irritation or injury and thus not to evoke a clinically significant immune response. The polymer may be selected so as to allow a balloon driven expansion. Such an expandable medical device would comprise a thermal balloon or non-thermal balloon wherein the medical device can have a structure which is crimpable during loading and expandable without stress crazing in physiological conditions. Advantageously, the polymer composition may be selected to orient and/or crystallize upon strain of deployment, for example during balloon dilation, in order to improve its mechanical properties.

By careful selection of polymer compositions and structural construct of the medical device, immunogenicity and inflammatory responses can be minimized. For example, if the device is shaped to lack protruding contours there may be precluded, or at least minimalized, polymeric and structural antigenicity so as to slow an immune response. Similarly, by selecting appropriate copolymers in the appropriate ratio, the resulting breakdown products of the polymers comprising a medical device may be more "friendly," or less irritating or immunogenic, to the host, such as, for example, the vascular wall. When the polymer composition is designed to elicit slow breakdown kinetics, tissue overload or other inflammatory responses at the site of implantation may be avoided.

Further disclosed herein is a method for making a bioabsorbable medical device of the present invention comprising: blending a crystallizable composition comprising a base polymer of poly L-lactide or poly D-lactide linked with modifying copolymers comprising poly L (or D)-lactide-co-Trimethylene-carbonate or poly L (or D)-lactide-co-ε-caprolactone in the form of block copolymers or as blocky random copolymers wherein the lactide chain length is sufficiently long enough to allow cross-moiety crystallization; molding the polymer composition to structurally configure said implant; and cutting the implant to form desired patterns.

Another method for fabricating a medical device of the present application comprises: preparing a biodegradable polymeric structure; designing said polymeric structure to be configured to allow for implantation into a patient; cutting said structure into patterns configured to permit traversing of the device through openings and to allow for crimping of the device (as described in co-pending patent application Ser. No. 11/781,225, filed concurrent herewith). Embodiments utilizing secondary meandering struts which are expanded to the crystallized hoop form (as described in co-pending patent application Ser. No. 11/781,225, filed concurrent herewith) are particularly useful in securing the scaffold implant in the organ space as the crystalline moiety is less rapidly degraded and bioabsorbed and therefore advantageously capable of maintaining position and integrity of the scaffold, thus preventing premature collapse and dangerous bulk break-up of the scaffold.

As is well understood in the art, the polymeric scaffolds of the above described embodiments may lack contrast to be detected by the currently available detection devices such as x-ray monitors. Therefore, the contrast detection enhancement of tissue implants by electron-dense or x-ray refractile markers is advantageous. Such markers can be found in biodegradable spot depots filled with radiopaque compositions prepared from materials known to refract x-radiation so as to become visible in photographic images (FIGS. 3-7). Suitable materials include without limit, 10-90% of radiopaque compounds or microparticles which can be embedded in biodegradable moieties, particularly in the form of paste like compositions deposited in a plurality of cup shaped receptacles located in preformed polymeric scaffold strut elements.

The radiopaque compounds can be selected from x-radiation dense or refractile compounds such as metal particles or salts. Suitable marker metals may include iron, gold, colloidal silver, zinc, magnesium, either in pure form or as organic compounds. Other radiopaque material is tantalum, tungsten, platinum/iridium, or platinum. The radiopaque marker may be constituted with a binding agent of one or more aforementioned biodegradable polymer, such as PLLA, PDLA, PLGA, PEG, etc. To achieve proper blend of marker material a solvent system is includes two or more acetone, toluene, methylbenzene, DMSO, etc. In addition, the marker depot can be utilized for an anti-inflammatory drug selected from families such as PPAR agonists, steroids, mTOR inhibitors, Calcineurin inhibitors, etc.

In one embodiment comprising a radioopaque marker, iron containing compounds or iron particles encapsulated in a PLA polymer matrix to produce a pasty substance which can be injected or otherwise deposited in the suitably hollow receptacle contained in the polymeric strut element. Such cup-like receptacles are dimensioned to within the width of a scaffold strut element. Heavy metal and heavy earth elements are useful in variety of compounds such as ferrous salts, organic iodine substances, bismuth or barium salts, etc. Further embodiments that may be utilized may encompass natural encapsulated iron particles such as ferritin that may be further cross-linked by cross-linking agents. Furthermore, ferritin gel can be constituted by cross-linking with low concentrations (0.1-2%) of glutaraldehyde.

The radioopaque marker may be applied and held in association with the polymer in a number of manners. For example, the fluid or paste mixture of the marker may be filled in a syringe and slowly injected into a preformed cavity or cup-like depression in a biodegradable stent strut through as needle tip. The solvents contained in the fluid mixture can bond the marker material to the cavity walls. The stent containing radiopaque marker dots can be dried under heat/vacuo. After implantation, the biodegradable binding agent can breakdown to simple molecules which are absorbed/discharged by the body. Thus the radiopaque material will become dispersed in a region near where first implanted.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Figure 2A:
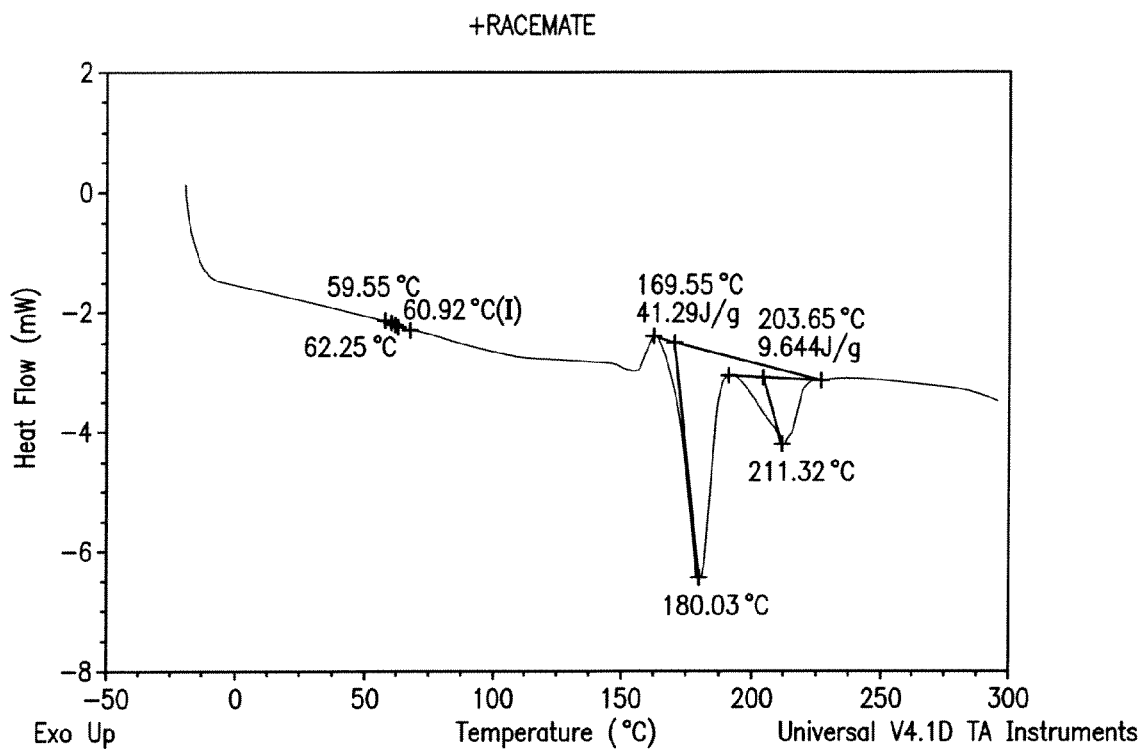
FIG. 2A and FIG. 2B depict DSC curves of polymer with racemate and without racemate formation, respectively: as illustrated racemate melt is shown to be significantly different in profile for the +racemate vs. the −racemate.
Figure 2B:
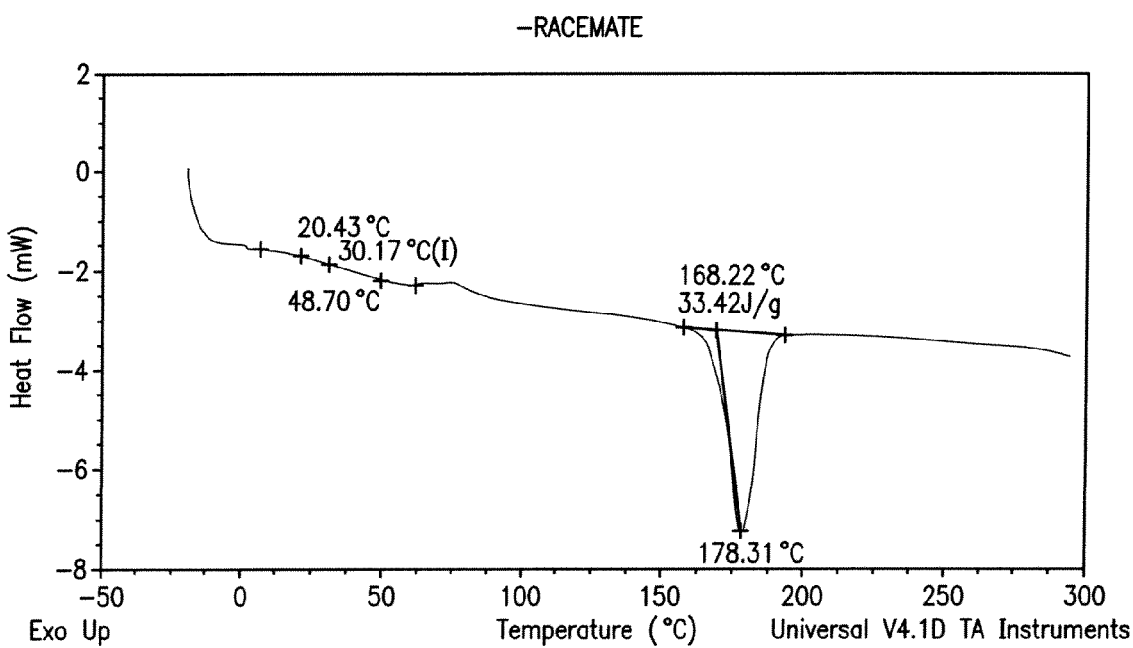

Now turning to the remaining figures:

FIG. 1 depicts change in modulus with recrystallization of LPLA/LPLA/TMC non-racemate blend versus a DPLA/LPA/TMC with only cross moiety racemate and a DPLA/LPLA/LPLA-TMC with additional racemate for formation;

FIG. 2A and FIG. 2B depict DSC curves of polymer with racemate and without racemate formation, respectively: as illustrated racemate melt is shown to be significantly different in profile for the +racemate vs. the −racemate.

FIGS. 3A-3G illustrate an embodiment method of radiopaque depot marking of a stent medical device: as seen in (a)-(d)) radiopaque material may be extruded into a cavity housed in the structure (g). As seen in cut-off views (e) and (f), such cavity may be a through-hole.

Figure 4A:
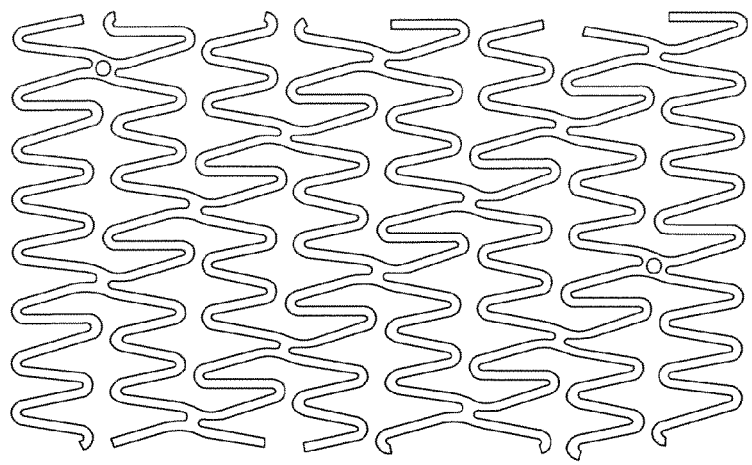
FIGS. 4A-4C illustrates different stent patterns of s scaffold with radiopague markers. As illustrated, the radiopaque markers can be placed at different locations on the stent patterns, while still allowing detection using radiopaque detection means.
Figure 4B:
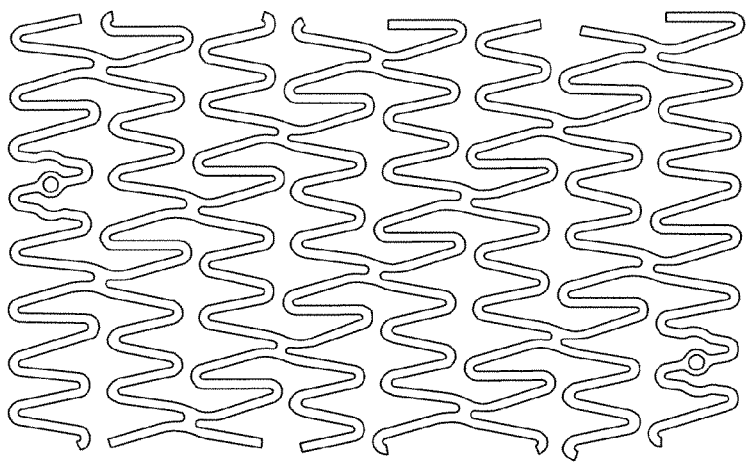
Figure 4C:
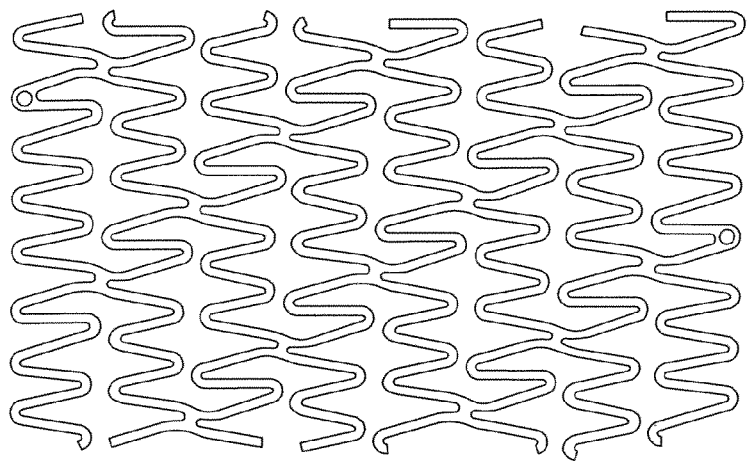

FIGS. 4A-4C illustrates different stent patterns of s scaffold with radiopague markers. As illustrated, the radiopaque markers can be placed at different locations on the stent patterns, while still allowing detection using radiopaque detection means.

Figure 5A:
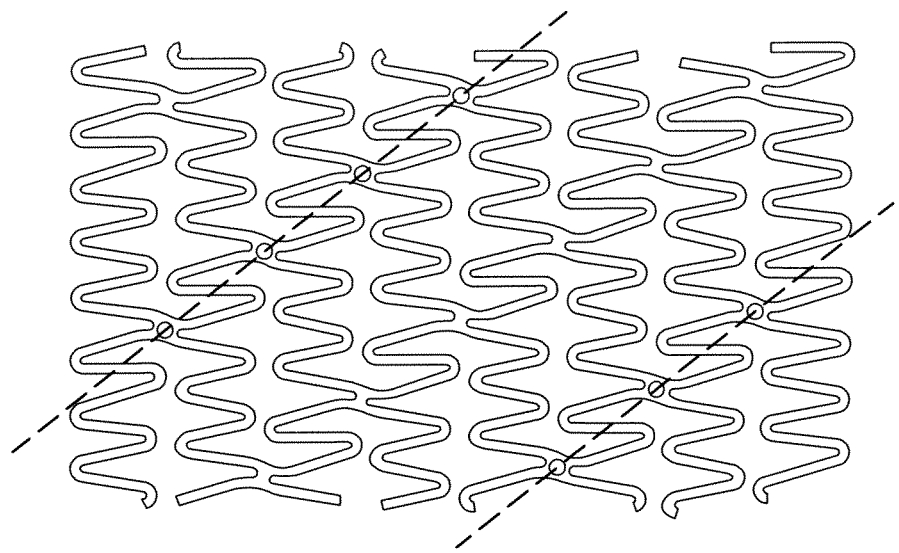
FIG. 5A and FIG. 5B illustrate a planar view of a stent material with radiopaque markers.
Figure 5B:
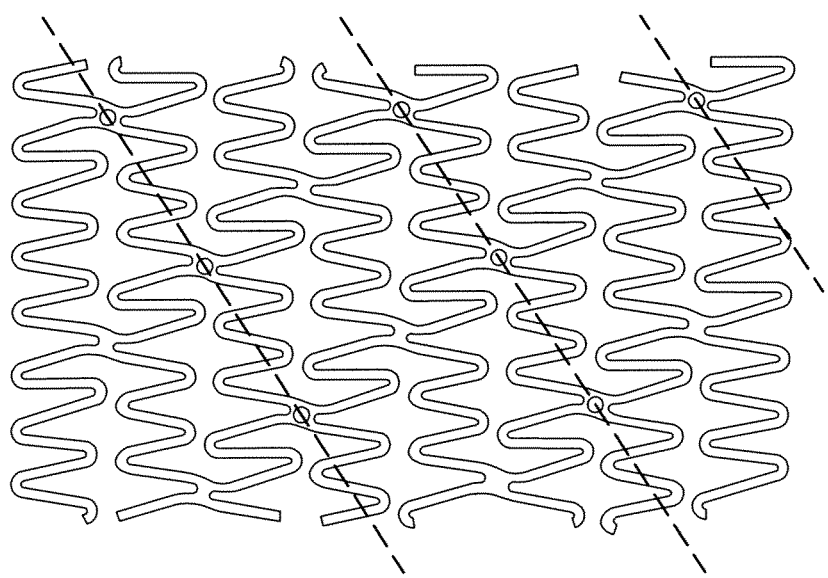

FIG. 5A and FIG. 5B illustrate a planar view of a stent material with radiopaque markers. As illustrated in FIGS. 5A and 5B the radiopaque markers can be aligned in the structure to allow for easier identification upon imaging or use of other detection methods.

Figure 6:
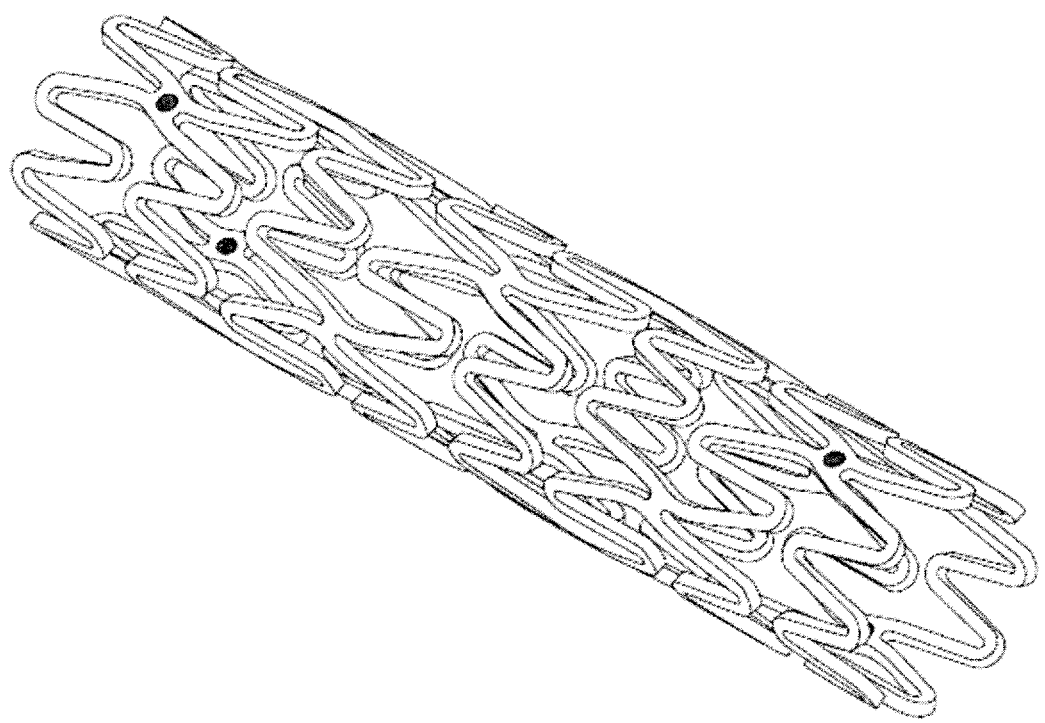
FIG. 6 shows an overview perspective of an actual stent with an embodiment radiopaque marker pattern, each located at a connection junction of the meandering strut.
Figure 7:
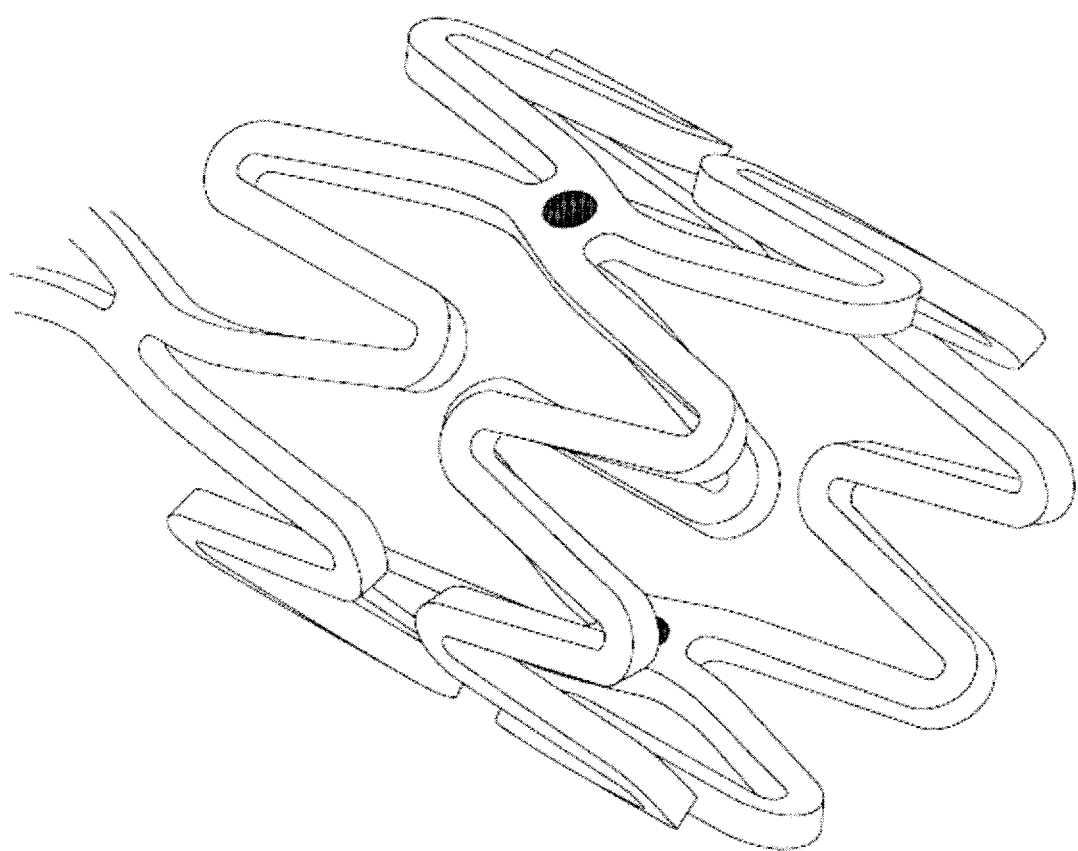
FIG. 7 shows a close-up view of a portion of the radiopaque marked stent of FIG. 6.

FIG. 6 shows an overview perspective of an actual stent with an embodiment radiopaque marker pattern, each located at a connection junction of the meandering strut. FIG. 7 shows a close-up view of a portion of the radiopaque marked stent of FIG. 6.

Figure 8:
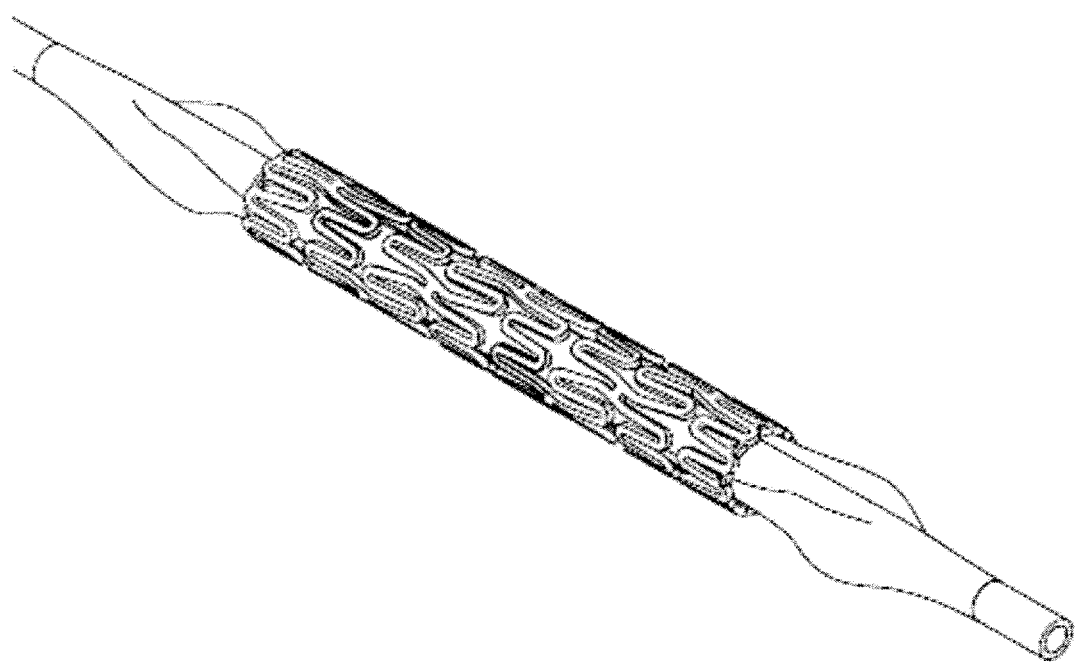
FIG. 8 shows in perspective view a stent embodiment of the present invention deployed on a balloon catheter.

FIG. 8 shows in perspective view a stent embodiment of the present invention deployed on a balloon catheter.

Figure 9:
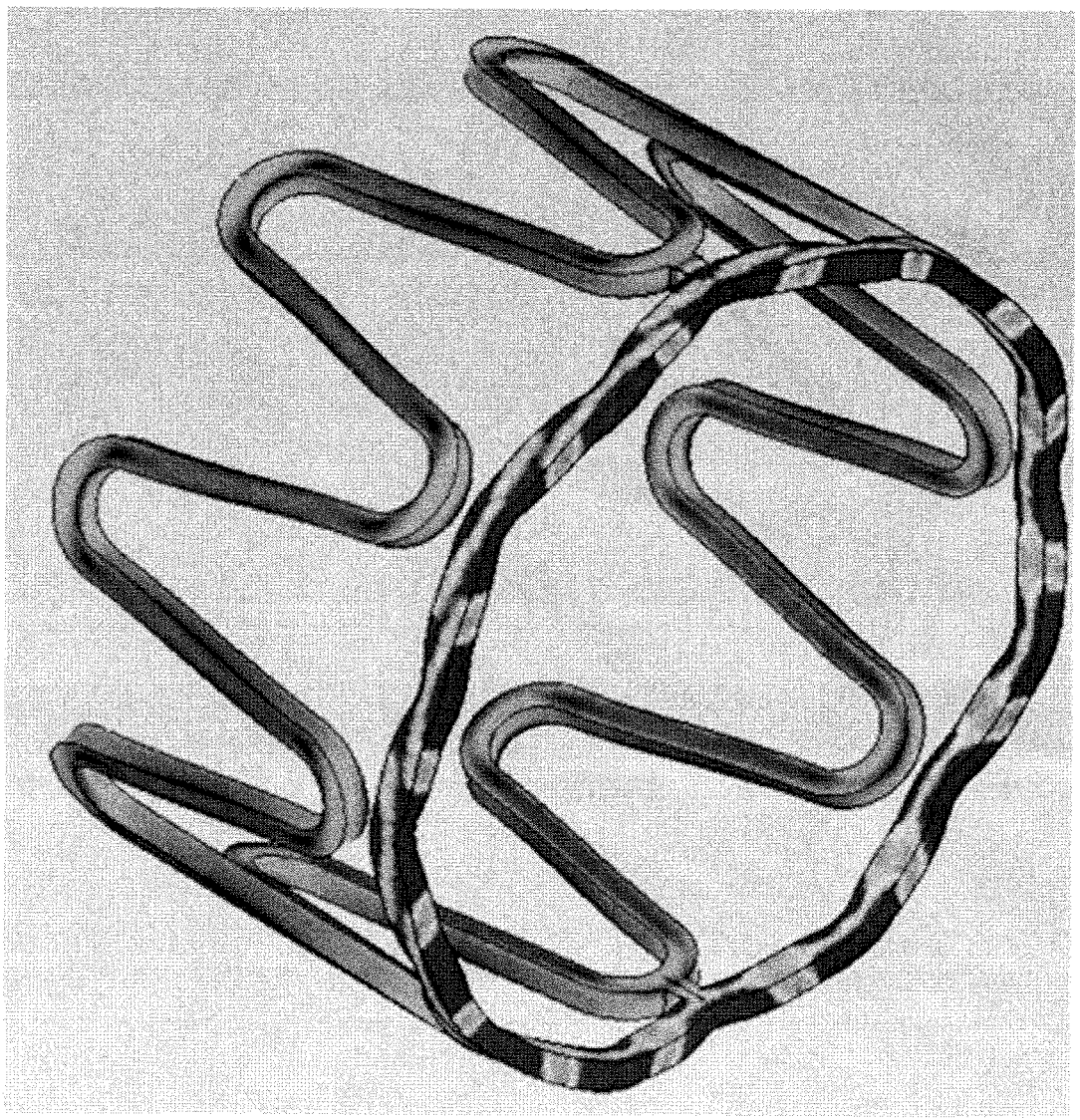
FIG. 9 depicts a fully expanded bioabsorbable scaffold stent comprising ring structuring showing fully crystallized holding rings or hoops.

FIG. 9 depicts a fully expanded bioabsorbable scaffold stent comprising ring structuring showing fully crystallized holding rings or hoops.

Figure 10A:
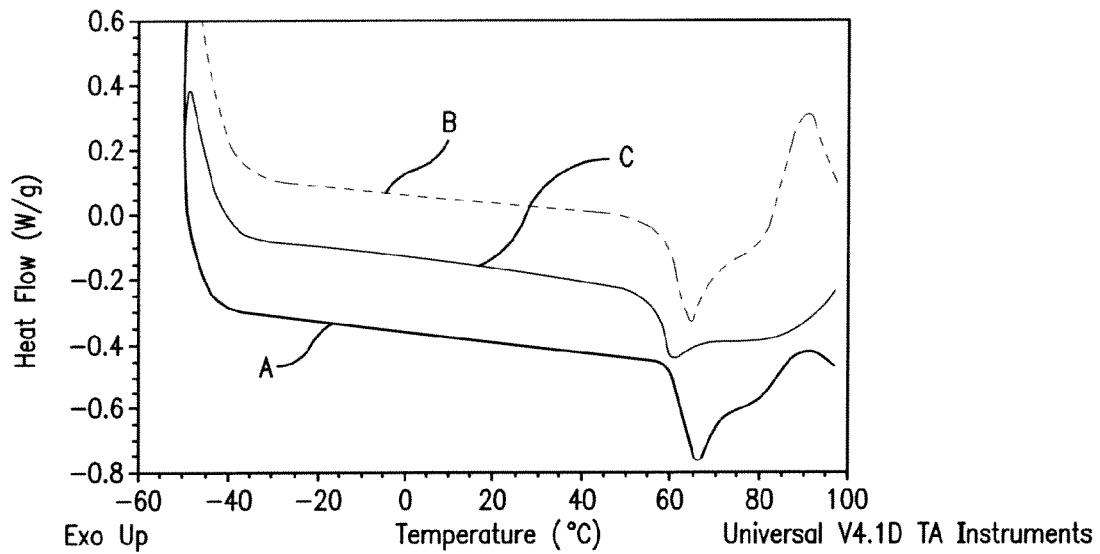
FIG. 10A and FIG. 10B illustrates DSC flow curves demonstrating single Tg and 10B shows a DSC flow curve showing double Tg.
Figure 10B:
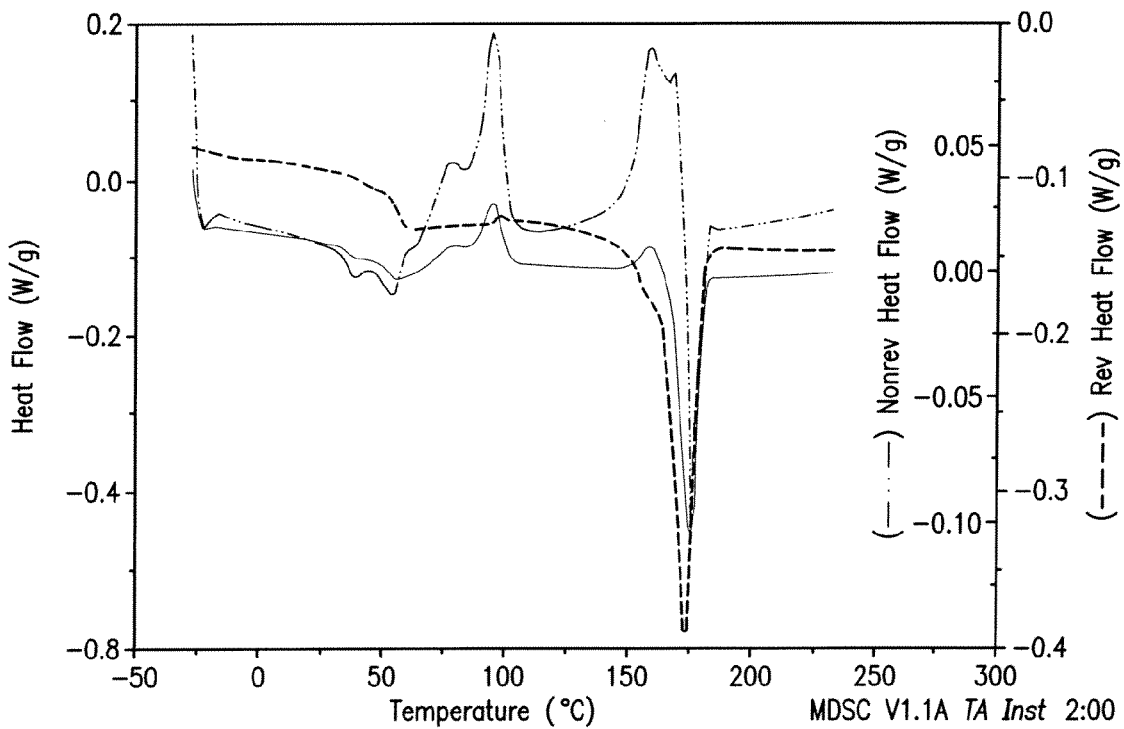

FIG. 10A and FIG. 10B illustrates DSC flow curves demonstrating single Tg and 10B shows a DSC flow curve showing double Tg.

Taking reference to FIG. 10A, polymer samples were analyzed for thermal transition temperatures using TA Instrument Q10 DSC. The samples were (A) Poly(L-co-DL-lactide) 70:30 copolymer, (B) Poly(L-lactide/Poly L-lactide-co-ϵ-caprolactone), and (C) Poly(L-lactide/Poly L-lactide-co-TMC). The polymers gave broad transition peaks at Tg's of 30° C. and 50° C., which were only present on the original run. Transition temperatures and curves of the later runs are given in the table below.

TABLE

| Polymer | Transition Temperature (C.) |
|---|---|
| PLDL 70/30 | 66 |
| LPLA/PCL Hybrid | 64 |
| LPLA/TMC | 61 |

Taking reference to FIG. 10B, other polymer samples (LPLA/TMC hybrid) were analyzed via DSC showing a double Tg.

What is claimed is:

1. A method for making a bioabsorbable stent comprising the steps of:
    (a) blending a polymer composition comprising a crystallizable bioabsorbable polymer composition, wherein the crystallizable bioabsorbable polymer composition comprises a base polymer comprising a poly(L-lactide) moiety and/or poly(D-lactide) moiety, and/or poly L-lactide-co-PEG moiety, and/or poly D-lactide-co-PEG moiety, linked with a modifying copolymer thereof comprising poly(L-lactide-co-Tri-methylenecarbonate) and/or poly(D-lactide-co-Tri-methylene-carbonate) and/or poly(L-lactide-co-ϵ-caprolactone) and/or poly (D-lactide-co-ϵ-caprolactone) in the form of block copolymers or as blocky random copolymers; wherein the chirality of the polylactide segments of the modifying copolymer are opposite to the chirality of the polylactide segments of the base polymer; and
    (b) molding or extruding said polymer composition to produce a tube, wherein the polymer composition forms a lactide racemate stereo complex crystal structure between the base polymer and the modifying polymer.

2. The method of claim 1, further comprising the step of cutting the tube into a scaffold form using a laser after step (b), wherein the scaffold form comprises a cage-like mesh of meandering struts connected to hoop-like rings.

3. The method of claim 2, wherein the hoop-like rings are positioned at at least one end of the tube.

4. The method of claim 2, wherein the hoop-like rings are positioned at the middle portion of the tube.

5. The method of claim 2, wherein the meandering struts comprise a first and second set of meandering struts, wherein (i) the first and second sets of meandering struts alternate in a pattern of first and second meandering struts, (ii) the second meandering struts form a hoop shape after expansion, and (iii) the crystallinity of the second meandering struts after expansion is greater than the crystallinity of the first meandering struts after expansion.

* * * * *